United States Patent
Ito et al.

(10) Patent No.: US 10,368,728 B2
(45) Date of Patent: Aug. 6, 2019

(54) ENDOSCOPE APPARATUS

(71) Applicant: OLYMPUS CORPORATION, Tokyo (JP)

(72) Inventors: Takeshi Ito, Hino (JP); Hiroyuki Kamee, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 267 days.

(21) Appl. No.: 15/334,887

(22) Filed: Oct. 26, 2016

(65) Prior Publication Data
US 2017/0042414 A1 Feb. 16, 2017

Related U.S. Application Data

(63) Continuation of application No. PCT/JP2015/062126, filed on Apr. 21, 2015.

(30) Foreign Application Priority Data

May 1, 2014 (JP) ................................ 2014/094844

(51) Int. Cl.
A61B 1/00 (2006.01)
A61B 1/05 (2006.01)
(Continued)

(52) U.S. Cl.
CPC ........ *A61B 1/0638* (2013.01); *A61B 1/00006* (2013.01); *A61B 1/00009* (2013.01);
(Continued)

(58) Field of Classification Search
None
See application file for complete search history.

(56) References Cited

U.S. PATENT DOCUMENTS

2004/0257438 A1* 12/2004 Doguchi ............ A61B 1/00009
348/65
2009/0036741 A1* 2/2009 Igarashi ............... A61B 1/0638
600/160
(Continued)

FOREIGN PATENT DOCUMENTS

CN 102327156 A 1/2012
CN 103582445 A 2/2014
(Continued)

OTHER PUBLICATIONS

International Search Report dated Jul. 28, 2015 issued in PCT/JP2015/062126.
(Continued)

*Primary Examiner* — Clifford Hilaire
(74) *Attorney, Agent, or Firm* — Scully, Scott, Murphy & Presser, P.C.

(57) ABSTRACT

The endoscope apparatus includes a light exit that radiates an illumination light constituted by narrow-band lights to an observation target, an image sensor that detects a reflected/scattered light from the observation target to output an imaging signal, and an image processing circuit that processes the imaging signal. The image processing circuit includes an estimator that associates, regarding each color sensitivity region of the image sensor, a peak wavelength of the narrow-band light with the intensity of the reflected/scattered light to derive narrow-band light spectral intensity information, estimating wavelength lacking region spectral intensity information, and a processor that performs wavelength lacking region correction processing on the basis of the narrow-band light spectral intensity information and the wavelength lacking region spectral intensity information so that the image signal will be closer to an image signal
(Continued)

obtained when an illumination light having no wavelength lacking regions is applied.

17 Claims, 19 Drawing Sheets

(51) Int. Cl.
    *A61B 1/06*     (2006.01)
    *A61B 1/07*     (2006.01)
    *H04N 9/04*     (2006.01)
    *G06T 7/90*     (2017.01)
    *G02B 23/24*     (2006.01)
    *H04N 5/225*     (2006.01)

(52) U.S. Cl.
    CPC ...... *A61B 1/00045* (2013.01); *A61B 1/00096* (2013.01); *A61B 1/051* (2013.01); *A61B 1/063* (2013.01); *A61B 1/0669* (2013.01); *A61B 1/07* (2013.01); *G02B 23/2469* (2013.01); *G02B 23/2484* (2013.01); *G06T 7/90* (2017.01); *H04N 5/225* (2013.01); *H04N 5/2253* (2013.01); *H04N 5/2256* (2013.01); *H04N 9/045* (2013.01); *G06T 2207/10024* (2013.01); *G06T 2207/10068* (2013.01); *H04N 2005/2255* (2013.01)

(56) References Cited

U.S. PATENT DOCUMENTS

| | | |
|---|---|---|
| 2011/0273548 A1 | 11/2011 | Uchiyama et al. |
| 2012/0184812 A1* | 7/2012 | Terakawa ........... A61B 1/00009 600/109 |
| 2012/0327205 A1* | 12/2012 | Takahashi ............ A61B 1/04 348/65 |
| 2013/0293693 A1 | 11/2013 | Igarashi et al. |
| 2013/0324797 A1 | 12/2013 | Igarashi et al. |
| 2016/0262626 A1* | 9/2016 | Pelosi ................ A61B 5/0059 |

FOREIGN PATENT DOCUMENTS

| | | |
|---|---|---|
| JP | H10-286235 A | 10/1998 |
| JP | 2012-020130 A | 2/2012 |
| JP | 5362149 B1 | 12/2013 |
| JP | 5427318 B1 | 2/2014 |
| WO | 2010/143692 A1 | 12/2010 |
| WO | WO 2012/098798 A1 | 7/2012 |

OTHER PUBLICATIONS

Chinese Office Action dated Jul. 14, 2017 in Chinese Patent Application No. 201580021920.4.

Japanese Office Action dated May 8, 2018 in Japanese Patent Application No. 2014-094844.

English translation of International Preliminary Report on Patentability dated Nov. 10, 2016 together with the Written Opinion received in related International Application No. PCT/JP2015/062126.

Japanese Office Action dated Feb. 5, 2019 in Japanese Patent Application No. 2014-094844.

\* cited by examiner

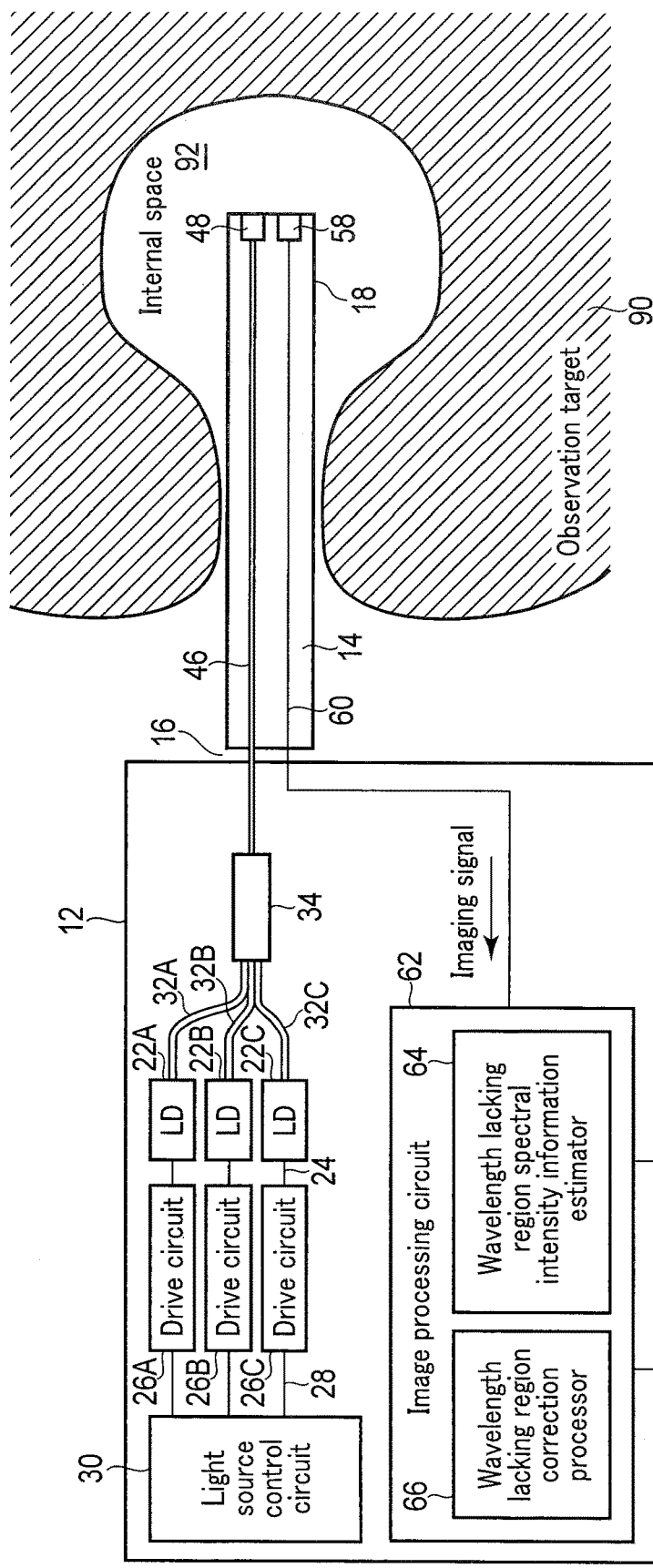
F I G. 1

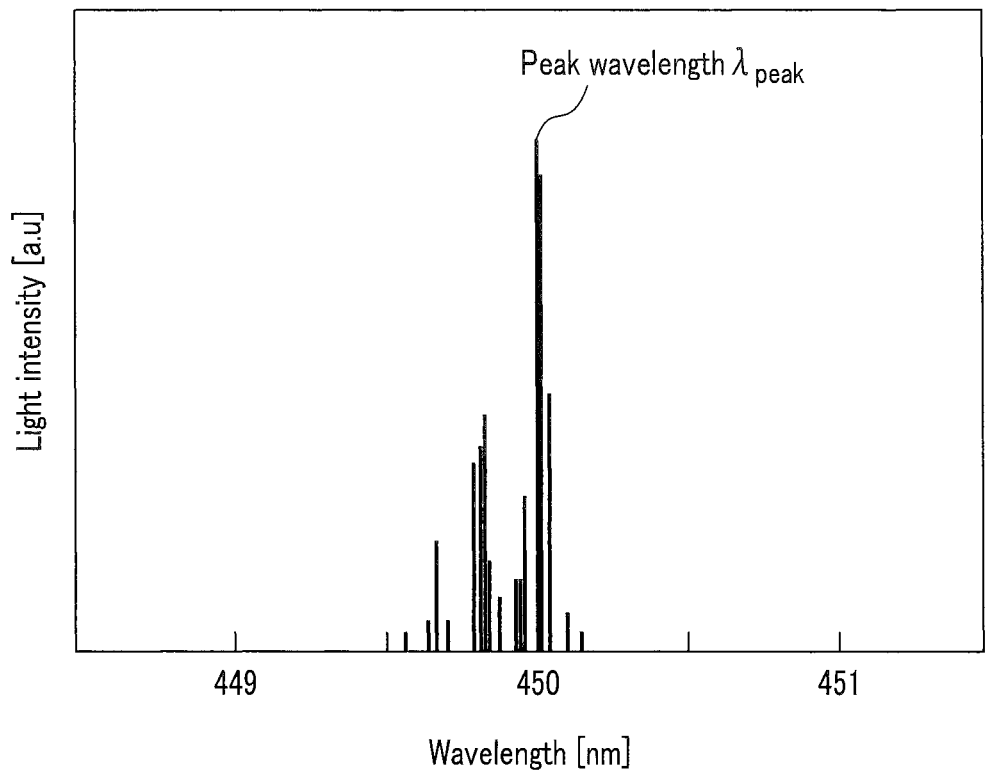
F I G. 2
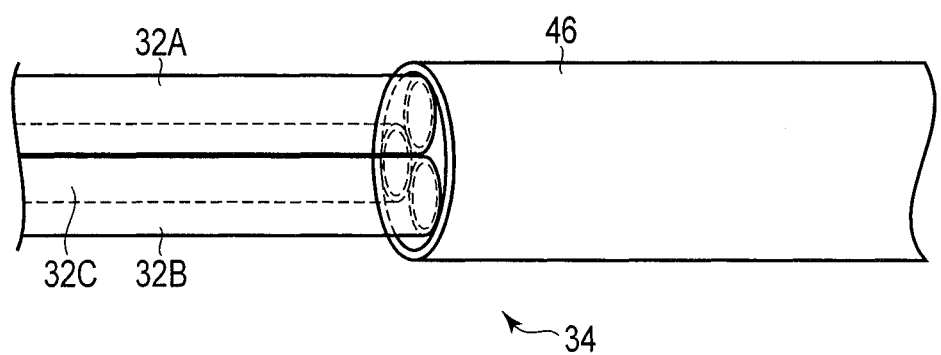
F I G. 3

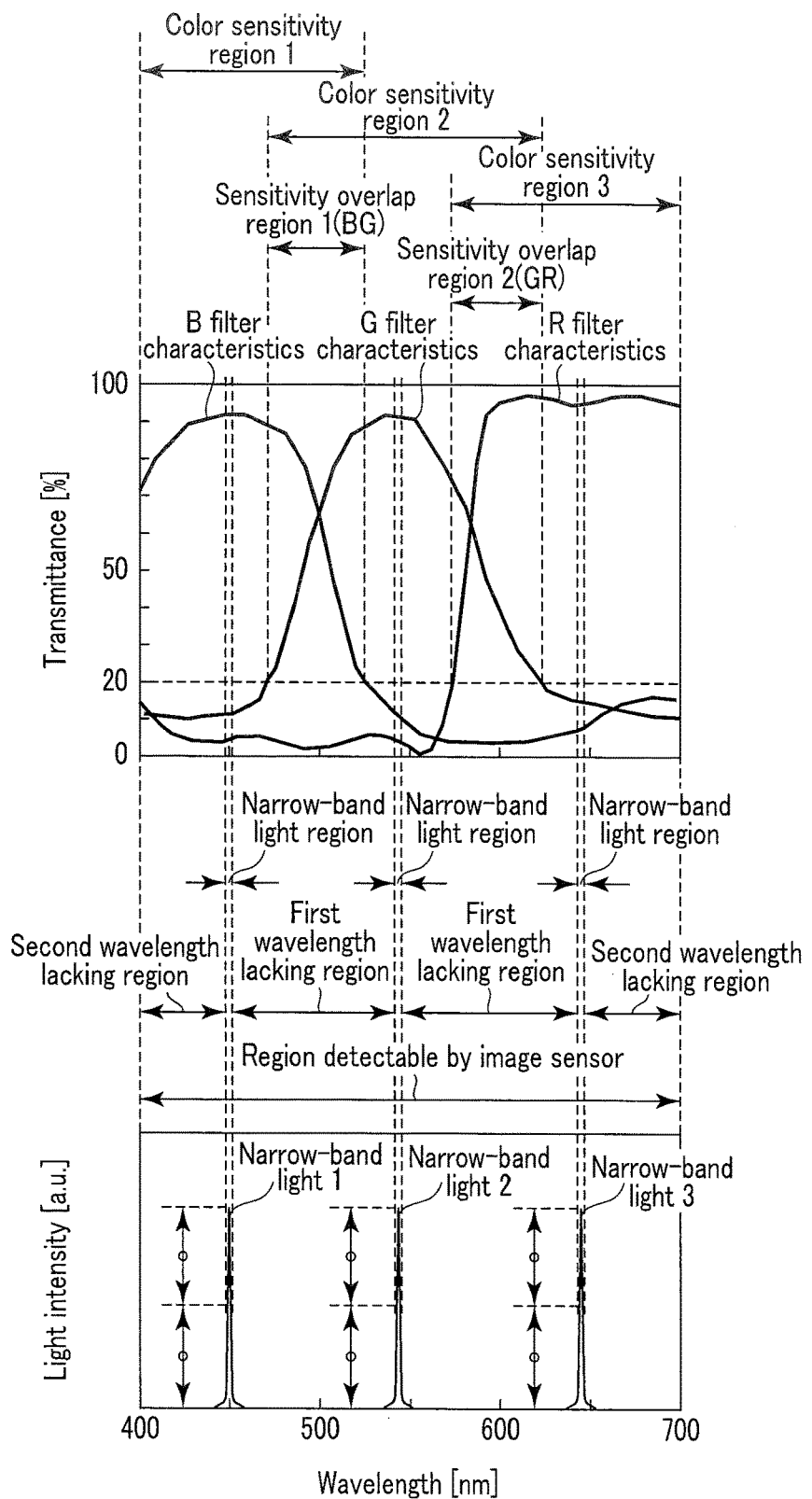
F I G. 6

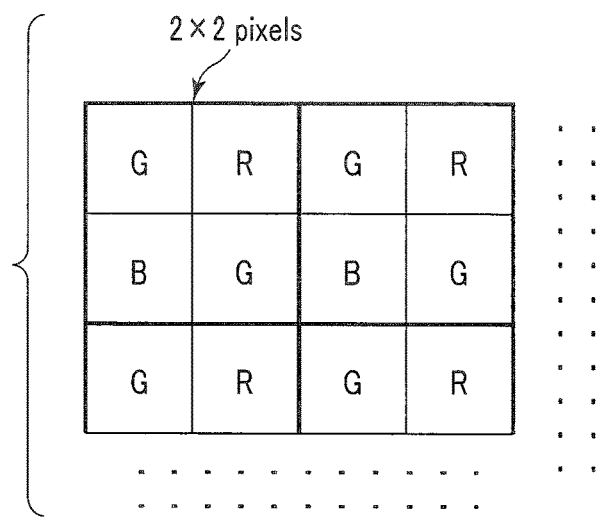
F I G. 9
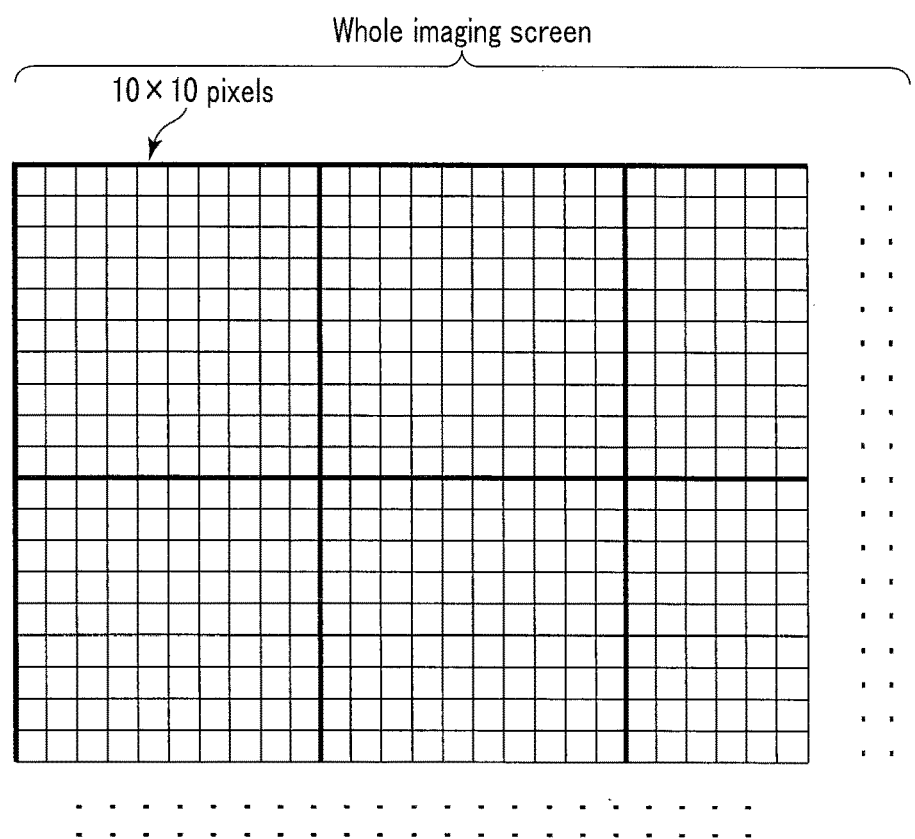
F I G. 10

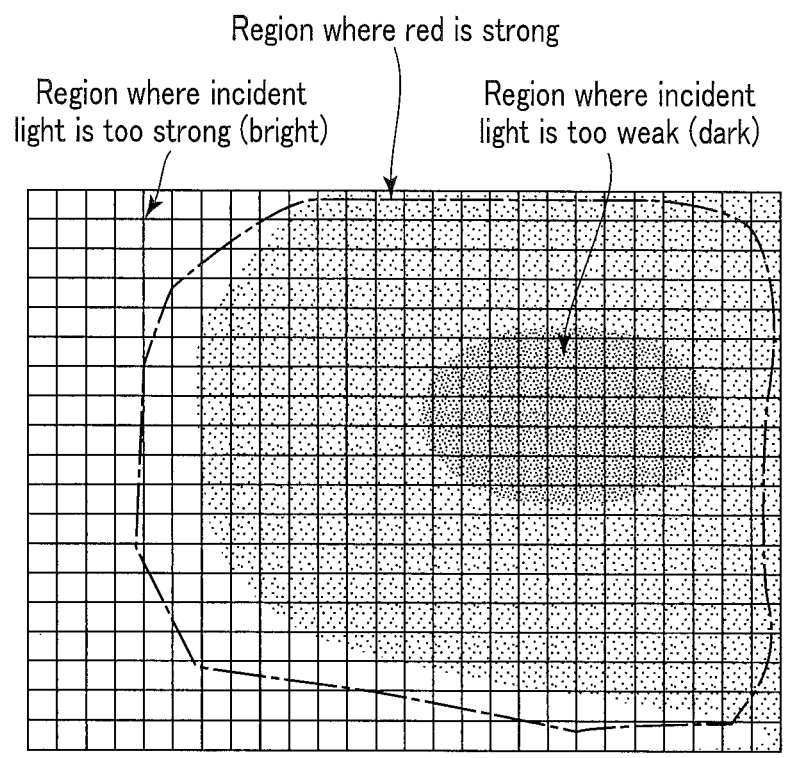
F I G. 11

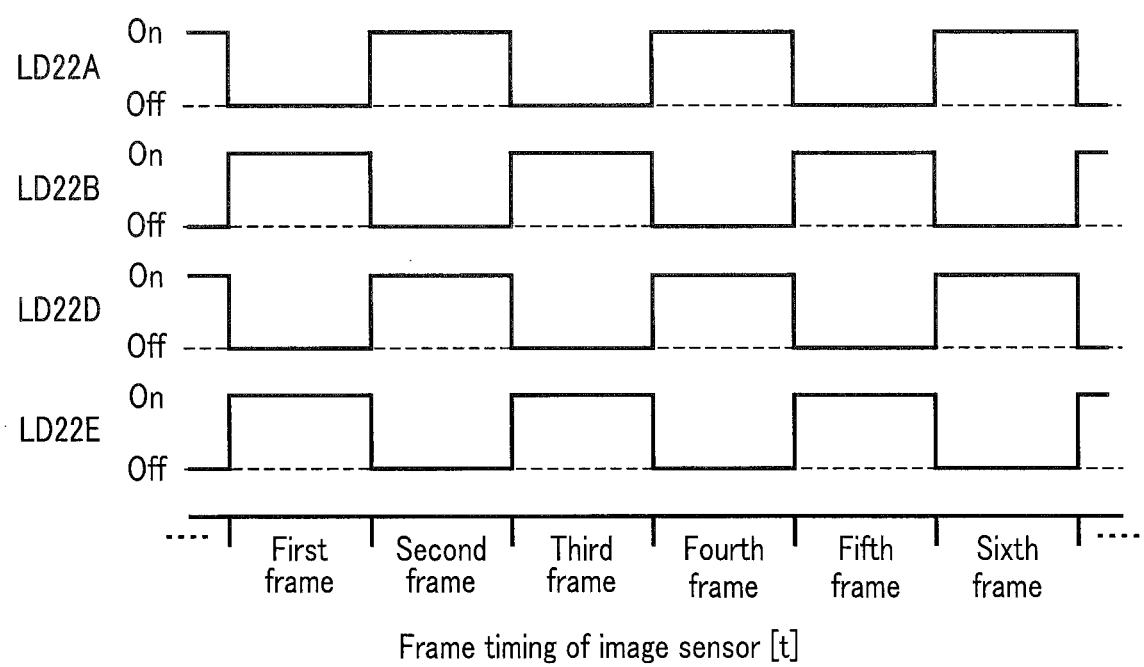
F I G. 16

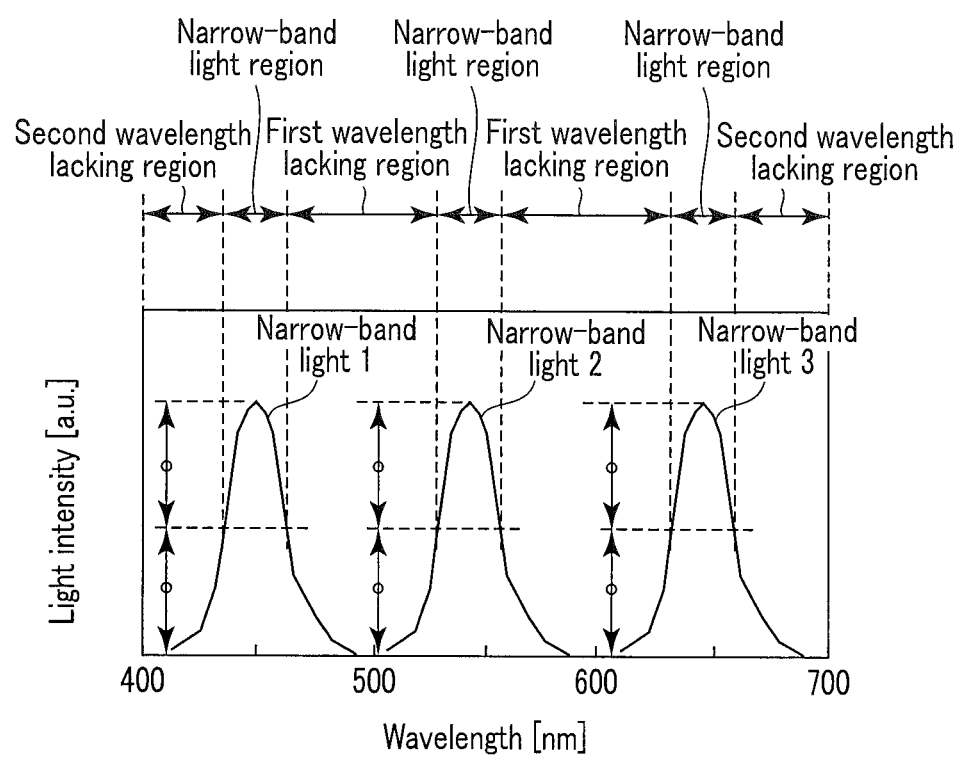
F I G. 20

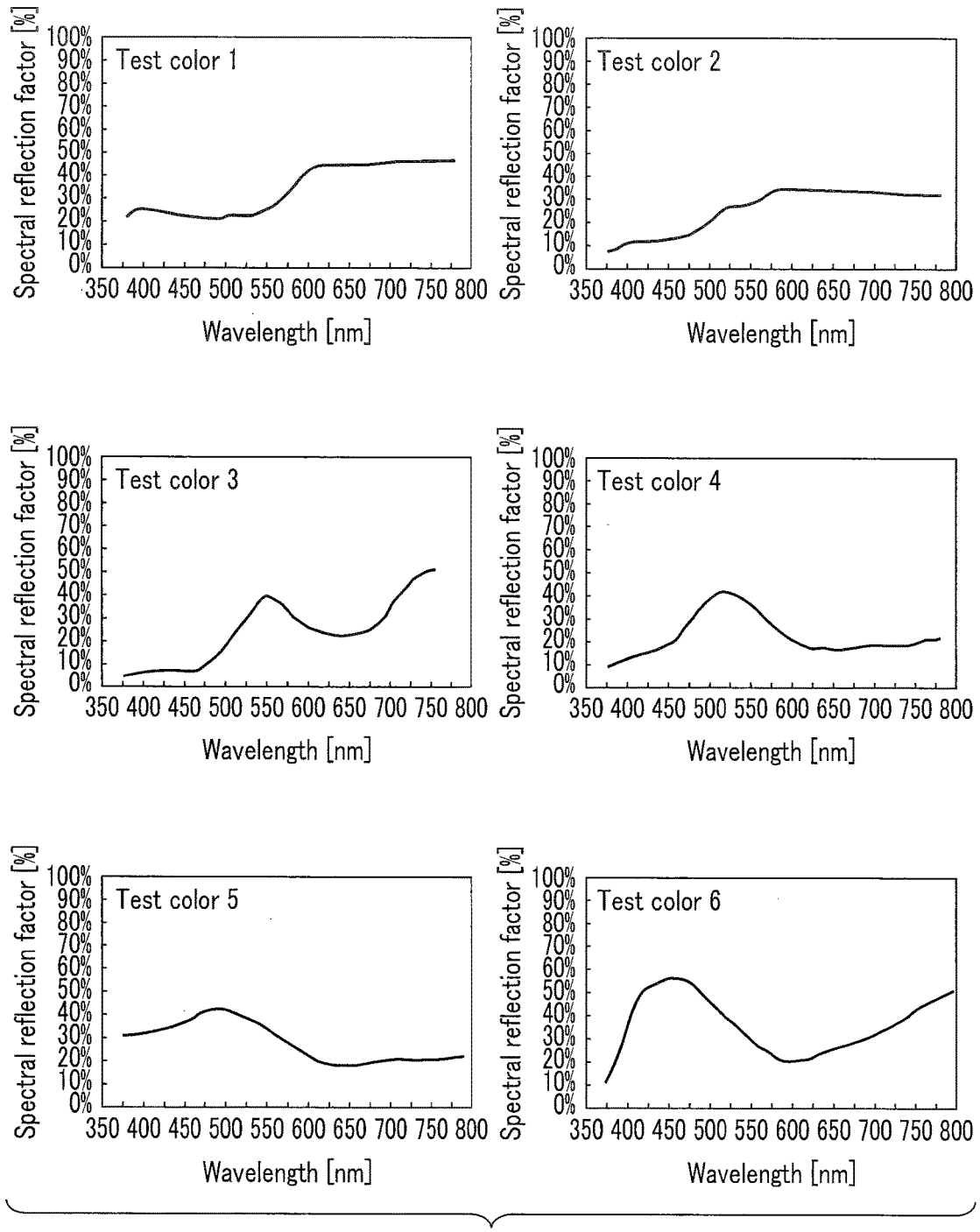
F I G. 21

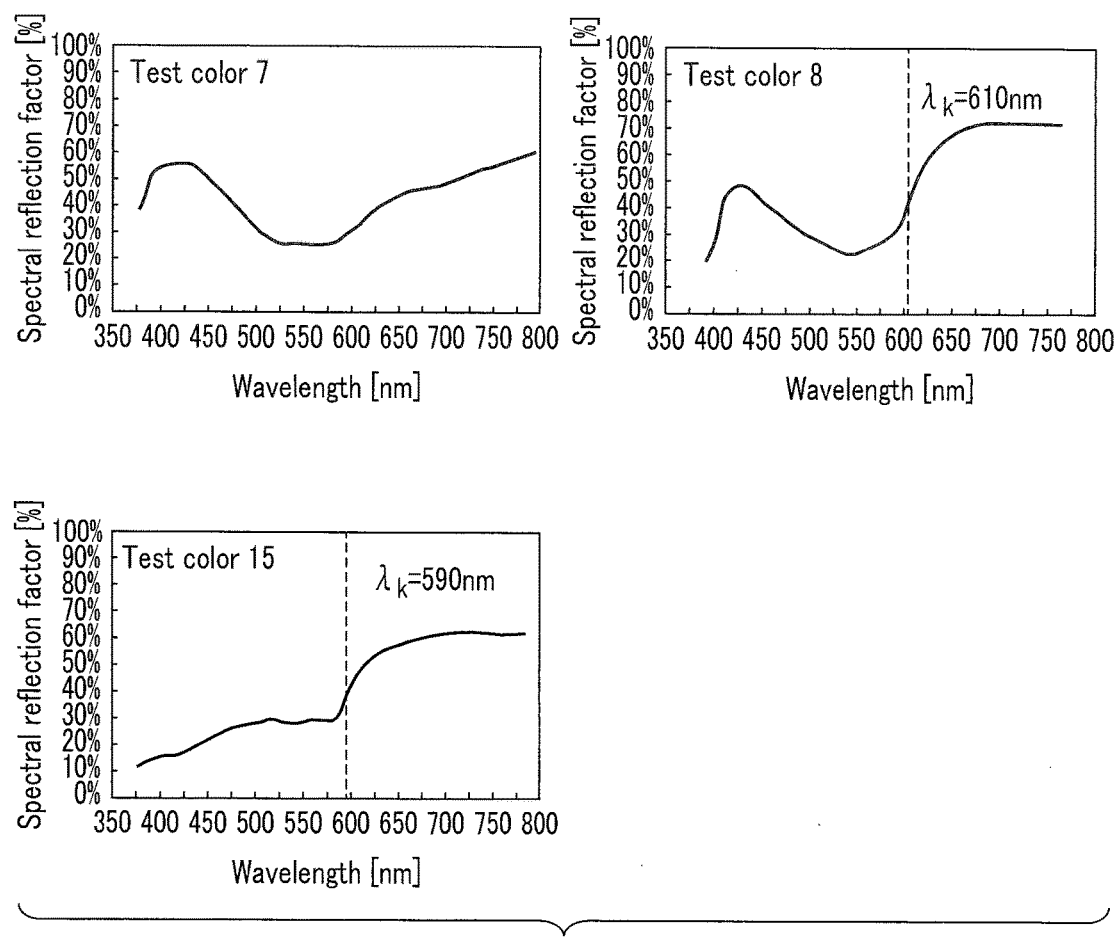
F I G. 22

ENDOSCOPE APPARATUS

CROSS-REFERENCE TO RELATED APPLICATIONS

This application is a Continuation Application of PCT Application No. PCT/JP2015/062126, filed Apr. 21, 2015 and based upon and claiming the benefit of priority from Japanese Patent Application No. 2014-094844, filed May 1, 2014, the entire contents of all of which are incorporated herein by reference.

BACKGROUND OF THE INVENTION

1. Field of the Invention

The present invention relates to an endoscope apparatus.

2. Description of the Related Art

At present, a so-called fiber light source in which small light sources are combined with optical fibers is developed. The fiber light source is suitably used as an illumination optical system of an observation apparatus such as an endoscope apparatus to observe an observation target from the distal end of a thin structure.

For example, Jpn. Pat. Appln. KOKAI Publication No. 10-286235 has suggested an endoscope apparatus equipped with a fiber light source in which laser light sources of three R, G, and B colors, optical fibers, and a diffusion plate are combined. The endoscope apparatus according to Jpn. Pat. Appln. KOKAI Publication No. 10-286235 is configured to guide, to the distal end of an endoscope through a light guide, laser lights from an He—Cd laser that is a three-primary-colors (white-light) laser to simultaneously oscillate a blue laser light of 441.6 nm, a green laser light of 537.8 nm, and a red laser light of 636.0 nm that are three primary colors, and from an He—Ne laser to emit a light having a red wavelength of 632.8 nm, and apply the laser lights to a living body that is an observation target through the diffusion plate and an illumination distribution adjustment filter.

In general, when a laser light is diffused and used as an illumination light, the problem is that there is a lack of information regarding lights that are not included in the wavelength of the laser light. That is, it is known that color reproducibility deteriorates when there is a difference of reflectivity of the living body that is an illumination target between the red laser light of 636.0 nm oscillated by the He—Cd laser and lights having neighboring wavelengths, and lights having other wavelengths in a red region. For example, when a light located in the vicinity of 636 nm is hardly reflected but the other lights in the red region are well reflected, the problem is that the illumination target appears dark under laser light illumination even though the illumination target actually appears red.

To address such problems, Jpn. Pat. Appln. KOKAI Publication No. 10-286235 has suggested that color reproducibility can be improved by the addition of the red light of 632.8 nm and that laser lights of multiple red wavelengths be combined.

BRIEF SUMMARY OF THE INVENTION

An endoscope apparatus according to the present invention includes an insertion portion having a distal end to be inserted into an internal space of an observation target, a light exit that radiates an illumination light to the internal space surface and that is provided at the distal end, an image sensor that detects a reflected/scattered light from the internal space surface to output an imaging signal and that is provided at the distal end, an image processing circuit that processes the imaging signal to output an image signal, and a display that displays an image in accordance with the image signal. The illumination light comprises narrow-band lights. Regions detectable by the image sensor comprise narrow-band light regions in which the respective narrow-band lights are present, a first wavelength lacking region that is a region between the adjacent two narrow-band light regions, and a second wavelength lacking region that is a region outside the endmost two narrow-band light regions. The image sensor includes a large number of light detection elements including multiple kinds of light detection elements to detect lights in multiple color sensitivity regions, respectively. The image processing circuit includes a wavelength lacking region spectral intensity information estimator that associates, regarding each color sensitivity region, a peak wavelength of the narrow-band light included in the color sensitivity region with the intensity of the reflected/scattered light from the internal space surface detected by the light detection element corresponding to the color sensitivity region to derive narrow-band light spectral intensity information (wavelength $\lambda$, light receiving intensity P), and estimates wavelength lacking region spectral intensity information on the basis of the narrow-band light spectral intensity information, the wavelength lacking region spectral intensity information being intensity information regarding the reflected/scattered light from the internal space surface in the first wavelength lacking region. The image processing circuit also includes a wavelength lacking region correction processor that performs wavelength lacking region correction processing on the basis of the narrow-band light spectral intensity information and the wavelength lacking region spectral intensity information so that the image signal will be closer to an image signal obtained when an illumination light having no wavelength lacking regions is applied.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 schematically shows an observation apparatus in a first embodiment;

FIG. 2 shows an example of a light emission spectrum of a semiconductor laser that emits a light having a wavelength of 450 nm;

FIG. 3 shows a connection portion of an optical-fiber type light combiner;

FIG. 6 shows the relation between color sensitivity regions, narrow-band light regions, and wavelength lacking regions in the first embodiment;

FIG. 9 shows 2×2 regions of four pixels that are a minimum unit in an image sensor having a Bayer array;

FIG. 10 shows the whole imaging screen to be a target for estimation and a region of 10×10 pixels;

FIG. 11 shows a taken image including regions where an incident light amount is too weak or too strong in the dynamic range of the image sensor;

FIG. 16 shows the relation between each semiconductor laser and frame timing in the third embodiment;

FIG. 20 shows an example of illumination lights in which three LED elements are combined;

FIG. 21 shows spectra of spectral reflection factors of test colors 1, 2, 3, 4, 5, and 6; and FIG. 22 shows spectra of spectral reflection factors of test colors 7, 8, and 15.

DETAILED DESCRIPTION OF THE INVENTION

First Embodiment

Figure 4:
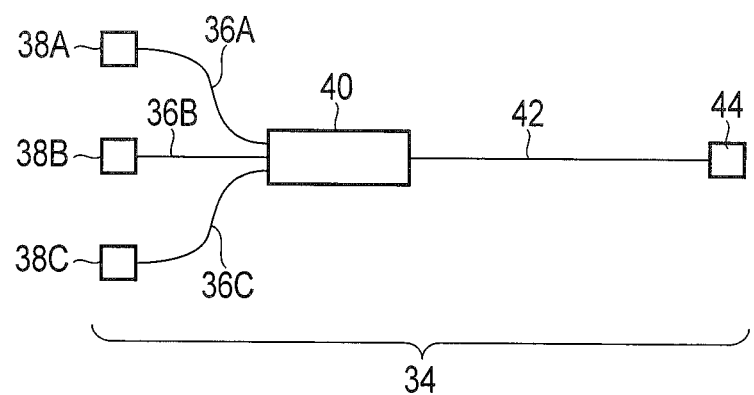
FIG. 4 shows an optical-fiber type light combiner in which an entrance side port and an exit side port are integrated.

Hereinafter, embodiments of an observation apparatus according to the present invention will be described in detail with reference to the drawings. The present invention is not limited by the embodiments below.

[Configuration]

FIG. 1 schematically shows an observation apparatus according to the present embodiment. As shown in FIG. 1, the present observation apparatus, which is, for example, an endoscope apparatus, comprises a body portion 12 including a light source portion, an insertion portion 14 having a distal end 18 to be inserted into an internal space 92 of an observation target 90, and a display 20 that displays an image of the surface of the internal space of the observation target 90.

The body portion 12 is equipped with three semiconductor lasers (LD) 22A, 22B, and 22C different from one another in emission wavelength, drive circuits 26A, 26B, and 26C that respectively drive the corresponding semiconductor lasers 22A, 22B, and 22C, a light source control circuit 30 that controls the semiconductor lasers 22A, 22B, and 22C through the drive circuits 26A, 26B, and 26C, three optical fibers 32A, 32B, and 32C that respectively guide laser lights sent out from the semiconductor lasers 22A, 22B, and 22C, a light combiner 34 that combines the laser lights guided by the three optical fibers 32A to 32C, and an optical fiber 46 that guides the laser lights combined by the light combiner 34.

The light source control circuit 30 and the drive circuits 26A, 26B, and 26C are connected to each other by control signal lines 28, and the drive circuits 26A, 26B, and 26C and the semiconductor lasers 22A, 22B, and 22C are respectively connected to each other by electric lines 24. The light source control circuit 30 is capable of controlling the amount of a laser light sent out from each of the semiconductor lasers 22A, 22B, and 22C and/or the on and off of each of the semiconductor lasers 22A, 22B, and 22C through the drive circuits 26A, 26B, and 26C. Although both the control signal lines 28 and the electric lines 24 are shown by single straight lines, multiple lines may be laid in practice. Moreover, obvious requirements such as a power supply cable are not shown.

The optical fiber 46 extends into the insertion portion 14 through a connection portion 16 of the insertion portion 14 and the body portion 12, and is optically connected to a light exit 48 provided at the distal end 18 of the insertion portion 14 located opposite to the body portion 12. The light exit 48 has a function to radiate the laser light guided by the optical fiber 46 to the surface of the internal space 92 of the observation target 90. Although the optical fiber 46 is configured to be attachable and detachable in the connection portion 16, an attachment/detachment mechanism is not shown for convenience, and both the body portion 12 side and the insertion portion 14 side of the attachment/detachment mechanism provided in the vicinity of the connection portion 16 are referred to as the optical fiber 46.

The distal end 18 of the insertion portion 14 is further provided with an image sensor 58 that detects a reflected/scattered light from the surface of the internal space 92 of the observation target 90 to output an imaging signal (an electric signal of imaging information). The image sensor 58 includes a large number of light detection elements including multiple kinds of light detection elements to detect lights in multiple color sensitivity regions, respectively. A signal line 60 that sends the imaging signal output from the image sensor 58 is connected to the image sensor 58, and the signal line 60 extends into the body portion 12 through a connection portion 16 of the insertion portion 14 and the body portion 12. An attachment/detachment mechanism is not shown for the signal line either, and a signal line that transmits a common signal is referred to as the signal line 60.

That is, the insertion portion 14 includes the light exit 48 and the image sensor 58 that are provided at the distal end 18, and partly includes the optical fiber 46 connected to the light exit 48 and the signal line 60 connected to the image sensor 58.

The signal line 60 extending within the body portion 12 is connected to an image processing circuit 62 that processes the imaging signal output from the image sensor 58 to output an image signal. That is, the body portion 12 further includes a part of the signal line 60 and the image processing circuit 62. The image processing circuit 62 includes a wavelength lacking region spectral intensity information estimator 64 and a wavelength lacking region correction processor 66 that will be described later.

The image processing circuit 62 is connected to the display 20 by a signal line 68. The image signal output from the image processing circuit 62 is sent to the display 20 through the signal line 68. The display 20 displays an image in accordance with the received image signal. An input section 70 to be input information for image processing is connected to the image processing circuit 62 by an electric line 72. Although both the signal line 68 and the electric line 72 are shown by single straight lines, multiple lines may be laid in practice.

The insertion portion 14 has an elongated and substantially circularly cylindrical appearance, and has a shape that is easily inserted into the internal space 92 of the observation target 90. In other words, the insertion portion 14 has a shape that facilitates the observation inside the internal space 92 of the observation target 90 having a narrow entrance, which is difficult to observe with a general observation apparatus. For example, as shown in FIG. 1, the internal space 92 of the observation target 90 can be a space that slightly spreads into the inner side from the narrow entrance, and it is difficult for an external light such as interior illumination and sunlight to come into such a space. Especially when the insertion portion 14 is inserted, the originally narrow entrance is further blocked by the insertion portion 14, and almost no external light comes in. That is, most of the illumination light in the internal space 92 of the observation target 90 is the illumination light sent out from the light exit 48 alone, and compared to the illumination light, the external light is almost negligible. The observation apparatus according to the present embodiment is suited to the observation of the internal space 92 in which external light is almost negligible compared to the illumination light.

<Semiconductor Lasers (LD)>

The semiconductor lasers are solid-state light sources that radiate laser lights when an electric current is passed through semiconductor elements. Semiconductor lasers of various wavelengths from ultraviolet light to infrared light are in practical use. The semiconductor lasers have advantages such as a small size and low power consumption, and have been actively developed for higher luminance and diversification of wavelengths in recent years. In general, the laser light is a light having wavelength characteristics of a line spectrum with an extremely small wavelength width. In the case of a semiconductor laser, the width of a spectral line (spectral line width) is generally 1 nm or less. The semiconductor lasers include, for example, an end face emitting type (stripe laser) that radiates a light from a cleavage plane of a wafer, and a surface emitting type (vertical cavity surface emitting laser; VCSEL) that radiates a light from the surface of a wafer. Also in practical use is a composite semiconductor laser typified by a second harmonic type (SHG semiconductor laser) in which nonlinear crystal is combined with an exit of a semiconductor laser to reduce an oscillation wavelength of the semiconductor laser by half.

The body portion 12 according to the present embodiment includes the three semiconductor lasers 22A, 22B, and 22C in ascending order of oscillation wavelength.

The semiconductor laser 22A is a multimode semiconductor laser that radiates a blue laser light having a wavelength of approximately 450 nm.

The semiconductor laser 22B is a multimode semiconductor laser that radiates a green laser light having a wavelength of approximately 540 nm.

The semiconductor laser 22C is a multimode semiconductor laser that radiates a red laser light having a wavelength of approximately 640 nm.

Each of the semiconductor lasers is a multimode laser. For example, as shown in FIG. 2, the multimode laser oscillates at multiple wavelengths, and the oscillation wavelengths from the shortest oscillation wavelength to the longest oscillation wavelength are included in a wavelength range of 1 nm or less. FIG. 2 shows an example of a light emission spectrum of the semiconductor laser 22A that radiates a light having a wavelength of 450 nm. The light emission spectrum has several ten line spectrum components, and the ratio and/or the number of line spectra change with time. The width of the wavelength region of the light emission spectrum has an expansion of approximately 1 nm in total. When the multimode laser light having such a spectrum is used as a narrow-band light, a peak wavelength $\lambda_{peak}$ of the narrow-band light is defined as a wavelength having the highest light intensity. In the present embodiment, a peak wavelength $\lambda_{peak}$ of the semiconductor laser 22A is equal to 450 nm. Similarly, a peak wavelength $\lambda_{peak}$ of the semiconductor laser 22B is equal to 540 nm, and a peak wavelength $\lambda_{peak}$ of the semiconductor laser 22C is equal to 640 nm.

As shown in the lower section of FIG. 6, regions that can be detected by the image sensor 58 and that have almost no laser lights are defined as wavelength lacking regions. Specifically, a region between two laser lights having adjacent wavelengths is defined as a first wavelength lacking region, and a region on the short wavelength side than the laser light having the shortest wavelength and a region on the long wavelength side than the laser light having the longest wavelength are defined as second wavelength lacking regions. More specifically, a narrow-band light region is assumed in the wavelength range of each laser light spectrum, so that a region between the narrow-band light regions of adjacent two laser lights is defined as the first wavelength lacking region, and a region on the short wavelength side than the narrow-band light region of the laser light having the shortest wavelength and a region on the long wavelength side than the narrow-band light region of the laser light having the longest wavelength are defined as the second wavelength lacking regions. Moreover, a region having intensity higher than ½ of the peak intensity of the laser light is the narrow-band light region. The wavelength lacking regions will hereinafter refer to a region that is a combination of the first wavelength lacking region and the second wavelength lacking region unless otherwise noted.

That is, in the present embodiment, the wavelength region detectable by the image sensor 58 is a wavelength region having a wavelength width of approximately 300 nm ranging from 400 nm to 700 nm. The wavelength region includes three narrow-band light regions having a width of 1 nm or less, and other regions of 297 nm or more are wavelength lacking regions. That is, 99% or more of the wavelength regions detectable by the image sensor 58 are wavelength lacking regions.

<Drive Circuits>

The drive circuits 26A, 26B, and 26C have functions to apply suitable electric currents to the respective semiconductor lasers 22A, 22B, and 22C, and have functions to switch on/off the semiconductor lasers 22A, 22B, and 22C and/or to control their light emitting state, for example, pulse-light the semiconductor lasers 22A, 22B, and 22C, on the basis of a control signal output from the light source control circuit 30 through the control signal lines 28. In addition, the drive circuits 26A, 26B, and 26C have functions to prevent the semiconductor lasers 22A, 22B, and 22C from being electrically broken by a rapid electric current increase or by the application of a nonstandard electric current or voltage. Moreover, the drive circuits 26A, 26B, and 26C have various functions of general semiconductor laser drive circuits.

<Light Source Control Circuit>

The light source control circuit 30 has a function to control the semiconductor lasers 22A, 22B, and 22C in relation to one another, and also independently control the semiconductor lasers 22A, 22B, and 22C.

For example, when the above three semiconductor lasers 22A, 22B, and 22C are combined, a substantially white light is produced if the three semiconductor lasers 22A, 22B, and 22C emit lights with substantially equal intensity. When the color of the illumination light needs to be adjusted to the purpose of illumination, illumination lights of various colors can be obtained if the light amount ratio of the semiconductor lasers 22A, 22B, and 22C is properly adjusted. The light source control circuit 30 according to the present embodiment can simultaneously increase or decrease the amounts of all the laser lights while maintaining a constant light intensity ratio of the laser lights of the three semiconductor lasers 22A, 22B, and 22C. The light source control circuit 30 can also independently increase or decrease the amount of a particular laser light alone, and turn on/off the particular laser light.

For example, if the light source control circuit 30 controls so that the whole light amount increases or decreases while a constant light amount ratio of the semiconductor lasers 22A, 22B, and 22C is maintained, the color of the illumination light does not change, and the brightness of the illumination light alone can be increased or decreased. If the light amounts of the semiconductor lasers 22A, 22B, and 22C are independently adjusted, the color of the illumination light can be variously adjusted. Moreover, if all the semiconductor lasers 22A, 22B, and 22C are simultaneously flashed, a light source portion that flashes in a desired color can be obtained. If the semiconductor lasers 22A, 22B, and 22C are sequentially flashed by different timings, a light source portion that sequentially changes the color of the illumination light can be obtained.

Moreover, the light source control circuit 30 can be configured to be capable of various controls suitably for purposes.

<Optical Fibers>

In the present embodiment, the optical fibers 32A, 32B, 32C, and 46 are used to guide laser lights from the semiconductor lasers 22A, 22B, and 22C to the light combiner 34 and guide the laser lights from the light combiner 34 to the light exit 48. Moreover, an optical-fiber type light combiner 34, which will be described later, is used as the light combiner 34.

Various optical fibers that are in practical use are available as these optical fibers 32A, 32B, 32C, and 46. In the present embodiment, the multimode semiconductor lasers are used as the semiconductor lasers 22A, 22B, and 22C, so that the multimode type optical fibers are used as the optical fibers 32A, 32B, 32C, and 46 for efficient entry and guiding of the multimode laser lights. General multimode type optical fibers have a core diameter of several ten μm to approximately 200 μm. The core diameter of the optical fibers is preferably large to improve the incident light rate of the laser lights sent out from the semiconductor lasers 22A, 22B, and 22C, and is preferably small, on the other hand, for the ease of bending and diametrical reduction of the insertion portion 14. Therefore, the core diameter of the optical fibers is selected based on, for example, the spreads of the laser lights sent out from the semiconductor lasers 22A, 22B, and 22C, the optical structure of a connecting portion to optically connect the semiconductor lasers 22A, 22B, and 22C and the optical fibers 32A, 32B, and 32C, the thickness of the insertion portion 14, and optical input/output requirements of the later-described light combiner 34. In the present embodiment, an optical fiber having a core diameter of approximately 50 μm and a cladding diameter of approximately 125 μm is used as the optical fiber 46, which is mounted on the insertion portion 14 and guides the laser light to the light exit 48.

Not only optical fibers that are different in core diameter but also optical fibers having various characteristics are in practical use for each purpose. For example, optical fibers can be selected suitably to purposes in accordance with the degree of a numerical aperture NA based on a refractive index difference between a core and a cladding, or a cladding diameter and a covering structure of the outside of the cladding that affect the ease of bending and strength.

Optical fibers of various materials are available. It is also possible to use not only conventionally used optical fibers with glass cores/glass claddings but also optical fibers with plastic cores and plastic claddings that are widespread for short distance light transmission. For a greater refractive index difference between a core and a cladding, a compound optical fiber in which a glass core and a plastic cladding are combined can also be used. In the present embodiment, optical fibers having quartz cores and glass claddings, which are relatively high in optical durability, are used for the reason of the intensities and wavelengths of the lights to be used.

<Light Combiner>

The light combiner 34 is an optical element having a function to combine lights entering from multiple entrance ends at one exit end. An optical element capable of coupling laser lights from multiple lasers to one optical fiber can be used; for example, an optical element based on a spatial optical system in which a cross prism and a dichroic mirror are combined, or an optical fiber type optical element in which core portions of diametrically small optical fibers are connected to a core portion of one diametrically large optical fiber can be used. An example of the optical fiber type light combiner 34 is shown in FIG. 3.

FIG. 3 shows a connection portion of the optical fiber type light combiner 34. The example in FIG. 3 is the 3 in 1 out light combiner 34 in which the three entrance side optical fibers 32A to 32C connected to three input ports and the exit side optical fiber 46 connected to one input port are optically connected to each other so that their end faces are pressed to face each other. Although FIG. 3 is an image diagram that prioritizes clarity, the part located in the vicinity of the connecting portion is actually fusion-bonded or fixed by, for example, an adhesive agent, and the connecting portion is entirely covered with a cover or the like to improve the mechanical strength of the connecting portion. In the case of such an optical fiber type light combiner 34, optical fibers 36A, 36B, and 36C as entrance side ports and an optical fiber 42 as an exit side port may be integrated with a light combiner 40 as shown in FIG. 4. In this case, the part (covered with a cover or the like) located in the vicinity of the connecting portion alone may be referred to as a light combiner, or the part from connectors 38A, 38B, and 38C of the entrance side ports to a connector 44 of the exit side port may be referred to as a light combiner.

The light combiner 34 shown in FIG. 3 is configured so that the diameter of the exit side optical fiber 46 is larger than the diameter of each of the entrance side optical fibers 32A to 32C. Thus, the optical fibers having different diameters can be incorporated in the light source portion, or the exit side optical fiber 46 may be processed to be gradually thinner to gently taper off.

Although the example of the 3 in 1 out (which means three entrance ends and one exit end) light combiner 34 is shown in FIG. 3 and FIG. 4 in accordance with the configuration in the present embodiment, the light combiner is not limited to this. A 2 in 1 out light combiner and a multiple-in 1 out light combiner in which a large number of input side optical fibers are coupled to one optical fiber have been in practical use in accordance with purposes, and various such light combiners can be used. It is possible to adjust the number of entrance ends for purposes by connecting light combiners in series. For example, it is possible to configure a 3 in 1 out light combiner as a whole by connecting, to an entrance end of a 2 in 1 out light combiner, the exit end of another 2 in 1 out light combiner. It is also possible to configure light combiners of various types by connecting various light combiners in series or in parallel.

Furthermore, although the 1 out light combiner is only shown in the present embodiment, the light combiner is not limited to this. For example, it is possible to provide more than one light exit 48 at the distal end 18 by combining 2×2 optical couplers in which side surfaces of cores of optical fibers are optically connected. Thus, when the observation target 90 is rugged, an unshadowed and satisfactory observation image can be obtained. It is also possible to use various optical couplers such as 3×3 or more optical couplers independently or in combination with the light combiner.

<Light Exit>

The light exit 48 has a function to adjust, to an illumination purpose, the optical characteristics of the laser lights that are three narrow-band lights different in wavelength that have been sent out from the three semiconductor lasers 22A, 22B, and 22C and that have been brought into the optical fiber 46 by the light combiner 34, and radiate the laser lights as illumination lights. That is, the light exit 48 has a function to adjust the optical characteristics of the laser lights that are primary lights sent out from the light source portion, and radiate the laser lights as illumination lights.

If sent out as it is, the laser light may be dangerous to the human body depending on its radiation angle or on the light intensity per unit angle. Thus, it is necessary to increase the radiation angle of the laser light to a safe level or increase the size of a light emitting point.

Because of the degree of coherence length that is an optical characteristic of the laser light, that is, because of the height of coherency, what is known as speckle noise in which luminescent spots are randomly generated is generated when the laser light is applied to, for example, a scattering surface. The speckle noise not only causes discomfort such as a flickering feeling to an observer but also becomes the cause of inhibiting the observation of details of an observation target. Thus, it is necessary to decrease the coherency.

Moreover, the NA that is an index based on the refractive index difference between the core and the cladding of the optical fiber has wavelength dependence similar to that of the refractive index. The radiation angle of the laser light sent out from the exit end of the optical fiber depends on the NA, so that the radiation angle also has wavelength dependence. If the radiation angle varies from wavelength to wavelength, the problem is that concentric color unevenness is generated, and the color therefore appears different depending on the position of the illumination target. In order to eliminate the wavelength-to-wavelength difference of the radiation angle, it is necessary to adjust the radiation angle and light distribution.

Figure 5:
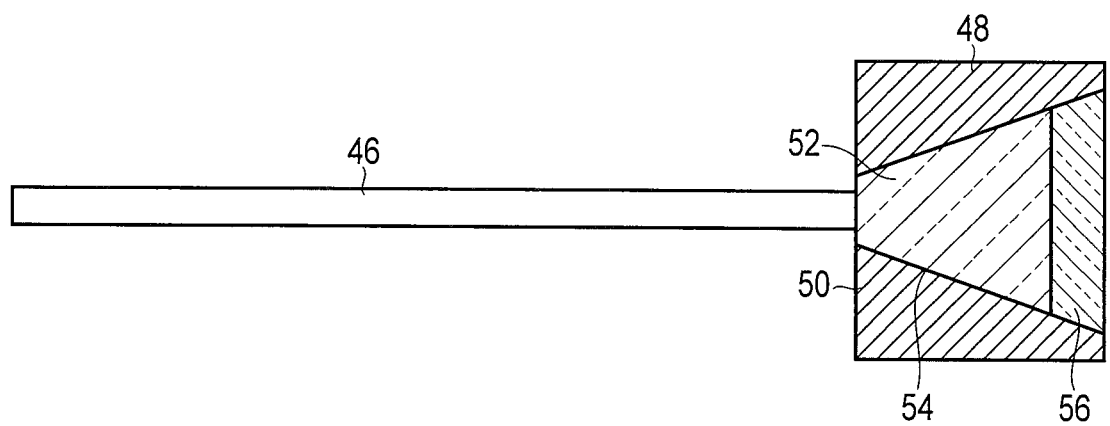
FIG. 5 shows the sectional structure of a light exit.

That is, for the various reasons described above, the light exit 48 has a function to adjust optical characteristics such as the radiation angle and the light distribution angle, the coherency, and the size of a light emitting point. In the present embodiment, the light exit 48 has a structure shown in FIG. 5. FIG. 5 shows the section of the light exit 48 cut along a plane that passes through the central axis of the distal end of the optical fiber 46. The light exit 48 includes a holder 50 having a truncated-cone-shaped through-hole. A reflecting mirror 54 is provided on the inner surface of the through-hole, and the inner surface determines a cavity 52. The cavity 52 is filled with a resin transparent to the laser lights sent out from the semiconductor lasers 22A, 22B, and 22C. The optical fiber 46 is connected to the cavity 52 at its small-diameter-side end, and a diffusion plate 56 is attached in the form of a lid to an opening of the through-hole of the holder 50 on the opposite side.

The optical fiber 46 and the holder 50 are assembled so as to keep an optical positional relation by unshown members such as a ferrule and a sleeve.

The laser light guided by the optical fiber 46 and sent out from the optical fiber 46 comes into the transparent resin in the cavity 52, travels while spreading with a spread angle corresponding to, for example, the NA of the optical fiber 46, the refractive index of the resin in the cavity 52, and the wavelength of the laser light, and enters the diffusion plate 56. For the diffusion plate 56, it is possible to use, for example, a transparent resin in which particles of, for example, alumina having a high refractive index are dispersed, a transparent resin in which structures such as minute air bubbles having, by contrast, a low refractive index are dispersed, frosted glass having minute depressions and projections on the surface, and a compound of the above. It is also possible to apply various members known as diffusion plates.

Some of the laser light that has entered the diffusion plate 56 is sent out to the outside through the diffusion plate 56, and the other is reflected/scattered backward and then travels. The laser light that has been reflected/scattered backward is reflected by the truncated-cone-shaped reflecting mirror 54, and again travels forward. Some of the light is sent out to the outside, and the other is again sent out backward. While a series of these operations are repeated, the laser light as a primary light that has entered the light exit 48 travels to the outside as an illumination light after the radiation angle, light distribution, and coherency that are the optical characteristics of the laser light are adjusted by the light exit 48. The size of the light emitting point is the size of the core portion of the fiber when the light exit 48 is not present, but is the size of the outer surface of the diffusion plate 56 after the passage of the light exit 48. That is, the size of the light emitting point becomes larger than the light exit 48.

According to the present embodiment, such a light exit 48 allows the distributions of the laser lights sent out from the semiconductor lasers 22A, 22B, and 22C to be substantially uniform, so that a evenly-colored, safe, low-coherency, and satisfactory illumination light can be obtained.

An image diagram of the spectra of the illumination lights sent out from the light exit 48 according to the present embodiment is shown in the lower section of FIG. 6.

As shown, the wavelength and intensity ratio of each laser light do not considerably change compared to the wavelengths and intensity ratio of the laser lights sent out from the semiconductor lasers 22A, 22B, and 22C, and the laser lights that are three narrow-band lights having substantially equal wavelengths and intensity ratios are sent out as illumination lights. That is, the wavelengths and the intensity ratio of the three laser lights are substantially equal when the primary lights are compared with the illumination lights.

The configuration of the light exit 48 shown here is only an example, and various modifications can be made. For example, it is possible to make various modifications; the entire light exit 48 may be slightly vibrated to sufficiently reduce coherency so that speckles are not easily produced, or another optical system for speckle measures according to a conventional art may be provided at the subsequent section of the light exit 48. It is also possible to provide two or more diffusion plates 56 or provide another diffusion plate at the subsequent section of the light exit 48. It is also possible to use an optical system such as a lens for fine adjustment of the light distribution and the radiation angle.

<Imaging System>

An imaging system comprises an imager that is the image sensor 58 provided at the distal end of the insertion portion 14, and the image processing circuit 62 provided inside the body portion 12. The imager and the image processing circuit are connected to each other by the signal line 60 (FIG. 1).

The observation apparatus according to the present embodiment has the insertion portion 14 inserted into the internal space 92 of the observation target 90, and is assumed to be used in an environment where the amount of external light such as natural light or room light is negligible compared with the amount of the illumination light. Therefore, the image sensor 58 acquires an image of the surface of the internal space 92 of the observation target 90 by the reflected/scattered light of the illumination light sent out from the light exit 48 toward the observation target 90. The image sensor 58 has a function to be able to acquire images separately and independently for the respective three wavelength regions: the red region (R region), the green region (G region), and the blue region (B region). That is, the image sensor 58 includes three kinds of light detection elements: R light detection elements to detect lights in the R region, G light detection elements to detect lights in the G region, and B light detection elements to detect lights in the B region. The R light detection elements, the G light detection elements, and the B light detection elements are light detection elements provided with R, G, and B filters having spectral characteristics shown in the upper section of FIG. 6, respectively. FIG. 6 shows an example of a general primary color filter for the image sensor 58. As in a widely used general image sensor 58, the R light detection elements, the G light detection elements, and the B light detection elements are arranged in large numbers in matrix form in the image sensor 58. The elements are, for example, in a Bayer array (not shown). The image sensor 58 has three kinds of light detection elements different in wavelength characteristics from one another.

As shown in the upper section of FIG. 6, each of the RGB filters has characteristics such that there is a high-transmittance region from which the transmittance gradually decreases. There are almost no regions where the transmittance is zero percent, and each filter has several percent to approximately 10 percent of transmittance remaining in the wide region of visible lights. In other words, each filter has approximately 5 to 20 percent of transmittance in regions other than the wavelength region that the image sensor 58 is intended to detect. That is, it can be said that the transmittance of this degree is at a negligible level for the purpose of color image photography. Thus, the region having 20 percent or more of transmittance exclusive of the above regions is defined as a sensitivity region of each light detection element. In this case, the sensitivity region of each light detection element in the present embodiment is, in the visible light region, as follows: the sensitivity region of the B light detection element ranges from 400 nm to 525 nm, the sensitivity region of the G light detection element ranges from 470 nm to 625 nm, and the sensitivity region of the R light detection element ranges from 570 nm to 700 nm. Further, a sensitivity overlap region is present between the light detection elements having adjacent wavelengths. A sensitivity overlap region 1 (BG) in the present embodiment is a region ranging from 470 nm to 525 nm, and a sensitivity overlap region 2 (GR) is a region ranging from 570 nm to 625 nm. The lights included in the sensitivity overlap regions are detected with sensitivities that are not negligible in the two light detection elements having adjacent wavelengths.

The general image sensor 58 is provided with an infrared cutoff filter to remove unnecessary infrared lights. In the present embodiment, an infrared cutoff filter to remove lights having a wavelength of 700 nm or more is provided. Thus, R filter characteristics in a color sensitivity region 3 shown in FIG. 6 show high transmittance near 700 nm, but the long-wavelength-side limit of the region that can be detected by the image sensor 58 is 700 nm.

In the general image sensor 58, the lower limit wavelength that can be detected by the material constituting the image sensor 58 is determined. A CCD or a C-MOS imager using a silicon semiconductor is used as the image sensor 58 used in the present embodiment. The short-wavelength-side detection limit of the image sensor 58 using the silicon semiconductor is approximately 400 nm. Thus, the short-wavelength-side limit of the region that can be detected by the image sensor 58 in the present embodiment is 400 nm.

FIG. 6 shows, in the present embodiment, the color sensitivity regions, the sensitivity overlap regions, and the wavelength relation among the wavelengths, the narrow-band light regions, and the wavelength lacking regions of the laser lights sent out from the three semiconductor lasers 22A, 22B, and 22C.

As shown in FIG. 6, in the present embodiment, a blue light having a wavelength of 450 nm sent out from the semiconductor laser 22A is included in the color sensitivity region 1 of blue transmitted through the B filter, a green light having a wavelength of 540 nm sent out from the semiconductor laser 22B is included in the color sensitivity region 2 of green transmitted through the G filter, and a red light having a wavelength of 640 nm sent out from the semiconductor laser 22C is included in the color sensitivity region 3 of red transmitted through the R filter. None of the light from the semiconductor laser 22A, the light from the semiconductor laser 22B, and the light from the semiconductor laser 22C are included in the sensitivity overlap regions.

In other words, the light detection element corresponding to the color sensitivity region 1 only detects the blue light having a wavelength of 450 nm from the semiconductor laser 22A, and does not detect other lights. Similarly, the light detection element corresponding to the color sensitivity region 2 only detects the green light having a wavelength of 540 nm from the semiconductor laser 22B, and does not detect other lights, and the light detection element corresponding to the color sensitivity region 3 only detects the red light having a wavelength of 640 nm from the semiconductor laser 22C, and does not detect other lights. Thus, if the color sensitivity region that only detects a single narrow-band light is defined as a single narrow-band light color sensitivity region, all the color sensitivity regions 1, 2, and 3 are single narrow-band light color sensitivity regions in the present embodiment.

The image sensor 58 is supplied with electric power through an unshown electric wire, and is instructed to start and end imaging. Under the instruction to start imaging, the image sensor 58 starts imaging, and receives the illumination light reflected/scattered by the surface of the internal space 92 of the observation target 90. Each light detection element of the image sensor 58 detects the imaging signal of each color sensitivity region on the basis of the wavelength characteristics of the combined filter, and transmits the imaging signal to the image processing circuit 62 through the signal line 60.

<Image Processing Circuit>

The image processing circuit 62 has a function to subject the received imaging signal to suitable image processing to convert the imaging signal into image information, and output the image information to the display 20 as an image signal.

The illumination lights sent out from the light exit 48 are three laser lights alone as shown in the lower section of FIG. 6, and wavelength lacking regions prevail throughout the region that can be detected by the image sensor 58. Thus, the image processing circuit 62 performs image processing to correct the wavelength lacking regions so that the image will be closer to an image obtained by the use of an illumination light having no wavelength lacking regions (a broadband light having a wavelength band spreading in the whole wavelength region that can be detected by the image sensor 58).

The image processing circuit 62 includes the wavelength lacking region spectral intensity information estimator 64 that estimates spectral intensity information regarding the wavelength lacking regions on the basis of the received imaging signal, and the wavelength lacking region correction processor 66 that makes a correction from the estimated wavelength lacking region spectral intensity information so that the image will be closer to the image obtained by the use of the illumination light having no wavelength lacking regions.

The wavelength lacking region spectral intensity information estimator 64 estimates lights reflected/scattered by the observation target 90 in the wavelength lacking regions from the light information regarding the illumination lights that are constituted by three laser lights and that have been reflected/scattered by the observation target 90. The flow is described in order on the basis of FIG. 7.

Figure 7:
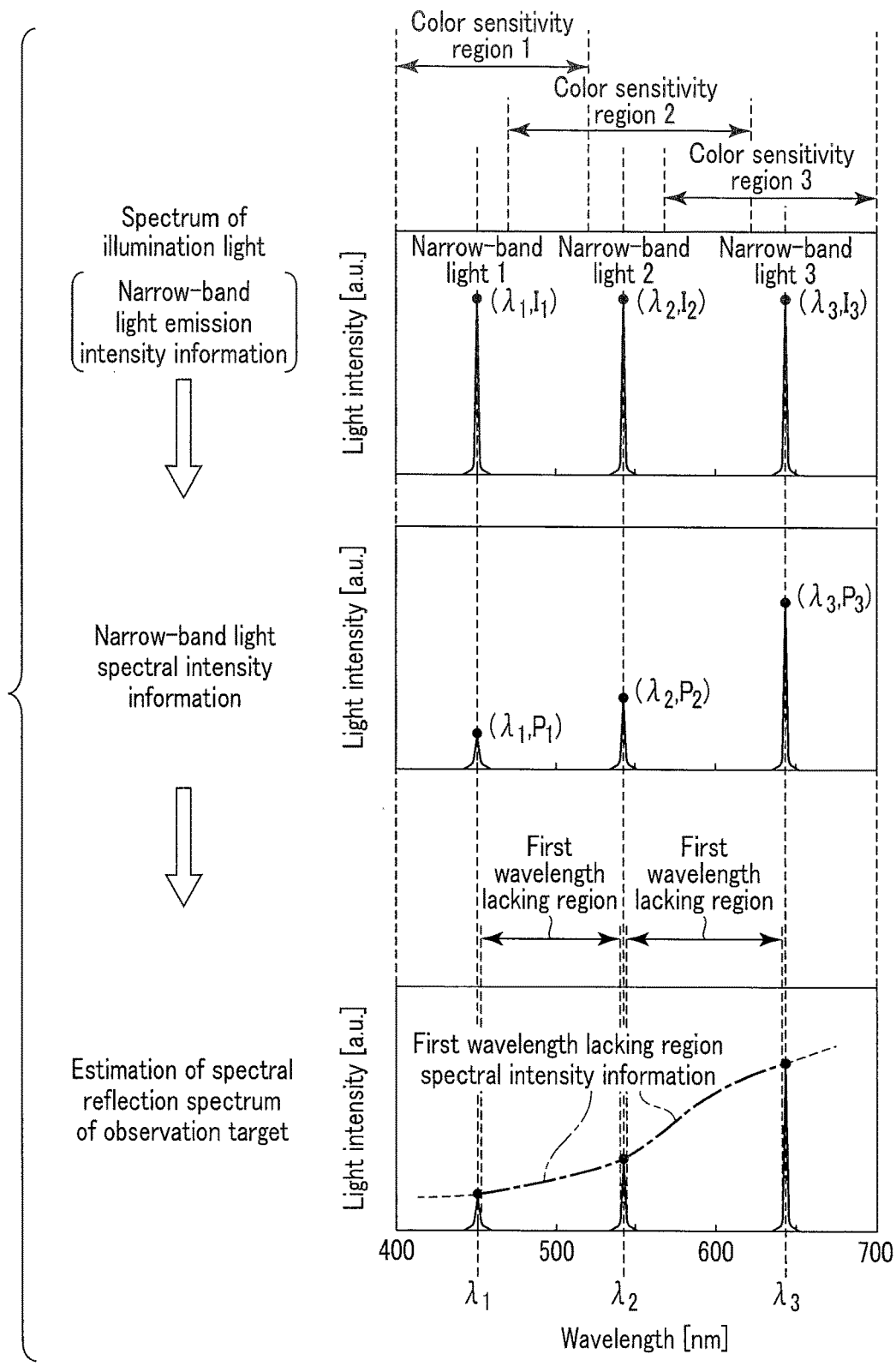
FIG. 7 shows narrow-band light emission information, narrow-band light spectral information, and estimated first wavelength lacking region spectral intensity information in the first embodiment.

The spectra of the illumination lights in the present embodiment are constituted by three narrow-band lights shown in the upper section of FIG. 7. That is, narrow-band light emission intensity information ($\lambda$, I) is determined from the peak wavelength of each laser light and its intensity. The narrow-band light emission intensity information (wavelength $\lambda$, light emission intensity I) can be set suitably to, for example, the use of the observation apparatus. In the present embodiment, the wavelengths of the three laser lights are, as described above, $\lambda_1$=450 nm, $\lambda_2$=540 nm, and $\lambda_3$=640 nm, respectively. Their intensity ratio is adjusted so that a nearly white light appears when all the lasers are turned on. That is, $I_1:I_2:I_3$=1:1:1.

When the illumination lights having such narrow-band light emission intensity information ($\lambda_1$, $I_1$), ($\lambda_2$, $I_2$), and ($\lambda_3$, $I_3$) are applied to the observation target 90, narrow-band light spectral intensity information (wavelength $\lambda$, light receiving intensity P) that is an imaging signal, for example, shown in the middle section of FIG. 7 is obtained. A method of deriving the narrow-band light spectral intensity information ($\lambda$, P) in actual scenes will be described later.

The wavelength lacking region spectral intensity information estimator 64 calculates wavelength lacking region spectral intensity information on the basis of the narrow-band light spectral intensity information ($\lambda_1$, $P_1$) ($\lambda_2$, $P_2$), and ($\lambda_3$, $P_3$). In the present embodiment, first wavelength lacking region spectral intensity information that is wavelength lacking region spectral intensity information regarding the first wavelength lacking region alone is estimated. That is, the wavelength lacking region spectral intensity information estimator 64 calculates, by interpolation, a hypothetical curve that smoothly and continuously connects the coordinates of three points of the narrow-band light spectral intensity information as shown in the lower section of FIG. 7 in a hypothetical graph in which the wavelength $\lambda$ is indicated on the horizontal axis and the light receiving intensity P is indicated on the vertical axis. A smoothing technique based on functional approximation is used to calculate the curve in the present embodiment. Commonly used various smoothing techniques such as approximation by a least squares method, approximation by a high-dimensional function, and approximation by a power function can be used as the functional approximation.

The curve of the first wavelength lacking region spectral intensity information that has been found in this way can be said to be an estimate of a spectrum in the case where the reflected/scattered light is spectrally detected by a spectroscope when a broad illumination light that is a broadband light having no wavelength lacking regions is applied to the observation target 90. The spectroscope referred to here means a photodetector capable of separately detecting light intensity per unit wavelength in a predetermined wavelength region.

Thus, by estimating the first wavelength lacking region spectral intensity information so that the narrow-band light spectral intensity information ($\lambda$, P) is smoothly and continuously connected, it is possible to obtain the first wavelength lacking region spectral intensity information close to that in the case where a broad illumination light is used. This is because most objects existing in nature such as living bodies have smooth and continuous and slightly uneven spectral reflection factors rather than a spectral reflection factor having sharp parts as in a line graph or a linear spectral reflection factor.

As described above, the wavelength lacking region spectral intensity information estimator 64 estimates the first wavelength lacking region spectral intensity information so that the narrow-band light spectral intensity information ($\lambda$, P) is smoothly and continuously connected.

Next, the function of the wavelength lacking region correction processor 66 is described.

From the first wavelength lacking region spectral intensity information estimated by the wavelength lacking region spectral intensity information estimator 64, the wavelength lacking region correction processor 66 estimates, for each color sensitivity region, light amount information $P_{estimate}$ to be received by the light detection element corresponding to each color sensitivity region of the image sensor 58 when the illumination light having no wavelength lacking regions is used. Further, the wavelength lacking region correction processor 66 compares light receiving intensity $P_{,\ detect}$ actually received by the light detection element corresponding to the color sensitivity region of the image sensor 58 with the estimated light amount $P_{,\ estimate}$, and calculates a correction value. The wavelength lacking region correction processor 66 processes the received imaging signal on the basis of the calculated correction value, and transmits the imaging signal to the display 20 as an image signal that is corrected light receiving amount information PP. As the corrected light receiving amount information PP that is an image signal close to that in the case where the illumination light having no wavelength lacking regions is applied for observation, the estimated light amount $P_{,\ estimate}$ may be used as it is, or a coefficient found from the comparison between $P_{,\ detect}$ and $P_{,\ estimate}$, and $P_{,\ detect}$ may be used in pairs. In the former case, a simple configuration having almost no processing load of the display 20 is possible. In the latter case, further fine adjustments can be made on the display 20 side. Moreover, in the latter case, when a correction is made in the whole imaging screen as will be described later, it is possible to simplify the information to be transmitted, by sending the ratio between $P_{,\ detect}$ and $P_{,\ estimate}$ as a piece of corrected light receiving amount information PP and transmitting $P_{,\ detect}$ for each pixel.

The processing in the wavelength lacking region correction processor 66 is described with reference to FIG. 8.

Figure 8:
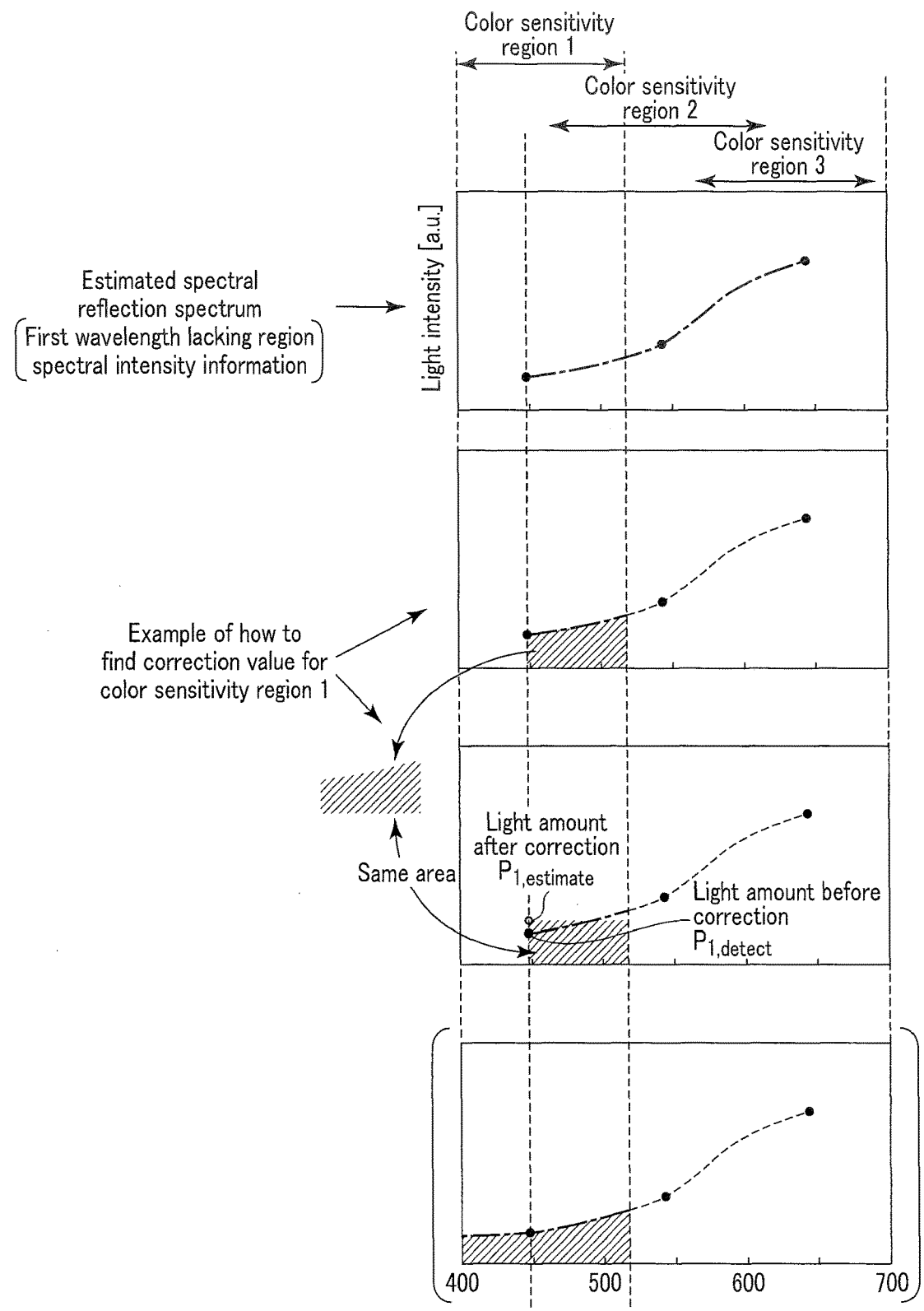
FIG. 8 shows an example of how to find a correction value for a color sensitivity region 1 on the basis of the estimated first wavelength lacking region spectral intensity information.

FIG. 8 is an image diagram showing the flow of the calculation of the above correction value on the basis of the first wavelength lacking region spectral intensity information estimated by the wavelength lacking region spectral intensity information estimator 64.

The uppermost section in FIG. 8 is a graph showing the first wavelength lacking region spectral intensity information as a spectral reflection spectrum estimated by the wavelength lacking region spectral intensity information estimator 64, in which the horizontal axis indicates the wavelength. The second section and the third section are image diagrams showing an example of how to find a correction value for the color sensitivity region 1.

When the spectral reflection spectrum shown in the uppermost section in FIG. 8 is estimated, the wavelength lacking region correction processor 66 integrates the spectral reflection spectrum with regard to the region that is within the wavelength region of the color sensitivity region 1 and in which an effective spectral reflection spectrum is present. In the example shown in FIG. 8, the wavelength lacking region correction processor 66 integrates the spectral reflection spectrum from the emission wavelength $\lambda_1=450$ nm of the semiconductor laser 22A to 525 nm that is the upper limit wavelength of the color sensitivity region 1, and finds the area of a substantially trapezoidal region that is shaded in the second section of FIG. 8. The wavelength lacking region correction processor 66 then calculates a rectangle shaded in the third section of FIG. 8 that has the same area as the shaded substantially trapezoidal region and in which has a width in the wavelength direction equal to that of the substantially trapezoidal region, thereby finding its height as a corrected light amount $P_{1,\ estimate}$. An image processing apparatus may send the value to the display 20 as an image signal without modification. Alternatively, it is also possible to calculate, for example, the value of $P_{1,\ estimate}/P_{1,\ detect}$ as a correction value, and use the value for other color regions of images obtained by other timings or simultaneously obtained images.

Although the color sensitivity region 1 of the image sensor 58 alone is described above, it is also possible to obtain $P_{2,\ estimate}$ and $P_{3,\ estimate}$ by performing similar processing for the color sensitivity regions 2 and 3.

Although the first wavelength lacking region spectral intensity information that is the spectral reflection spectrum is estimated for the first wavelength lacking region alone in the above explanation, second wavelength lacking region spectral intensity information can be estimated on the basis of a similar method. In this case, spectral reflection factor of the region can be found by extrapolation to estimate the second wavelength lacking region spectral intensity information. That is, it is only necessary to extrapolate by the aforementioned smoothing based on the functional approximation and estimate a spectral reflection spectrum for the whole second wavelength lacking region (the lowermost section in FIG. 8). At the time of the correction, the sensitivity of the imager, the characteristics of the filter, and the light emission spectrum of the light source may be taken into consideration.

As described above, according to the configuration in the present embodiment, it is possible to estimate light intensity that may be detected by the light detection element when the illumination light having no wavelength lacking regions is applied even if the illumination lights having wavelength lacking regions constituted by three laser lights are applied to the observation target 90. That is, when the intensity of the reflected/scattered light detected by the light detection element corresponding to the color sensitivity region 1 is $P_{1,\ detect}$ information regarding the intensity $P_{2,\ detect}$ of the reflected/scattered light detected by the light detection element corresponding to the color sensitivity region 2 and the intensity $P_{3,\ detect}$ of the reflected/scattered light detected by the light detection element corresponding to the color sensitivity region 3 is used in addition to the above information to estimate the spectral reflection spectrum of the observation target 90, so that light intensity that may enter the light detection element corresponding to the color sensitivity region 1 when the illumination light having no wavelength lacking regions is applied can be estimated.

<Image Region to Estimate Wavelength Lacking Region Spectral Intensity Information>

A narrow-band light intensity derivation region that is an image region to estimate the wavelength lacking region spectral intensity information is described next.

A series of estimations of the wavelength lacking region spectral intensity information described above can be performed by a minimum unit including the light detection element corresponding to the color sensitivity region 1, the light detection element corresponding to the color sensitivity region 2, and the light detection element corresponding to the color sensitivity region 3 of the image sensor 58. Here, the minimum unit refers to a unit that includes all color pixels of the image sensor 58 and that can form the whole imaging screen of the image sensor 58 by laying the unit. In the case of the image sensor 58 having a general Bayer array, four pixels of 2×2 in which one B pixel, one R pixel, and two G pixels are combined constitute the minimum unit. That is, four pixels of 2×2 can be used as the narrow-band light intensity derivation region.

In a general Bayer array, it is also possible to provide advantageous effects of the present invention by using only one of two G pixels even if single R, G, and B pixels are combined as the minimum unit. However, the information regarding the G pixel that is not included in the combination is not used, so that it can be said that using four pixels of 2×2 as the minimum unit is preferable.

In contrast, it is also possible to use the whole imaging screen of the image sensor 58 as the narrow-band light intensity derivation region. That is, it is also possible to extract a representative value by a method such as averaging with regard to the value of the light receiving intensity P of each of the light detection elements corresponding to the color sensitivity regions 1, 2, and 3 in the whole imaging screen of the image sensor 58, and use the value to estimate the wavelength lacking region spectral intensity information.

When an estimate is made for the minimum unit, the whole imaging screen can be finely corrected, so that the rate of improvement of color reproducibility is high, and the image can be closer to the image obtained by the use of the illumination light having no wavelength lacking regions. In contrast, when an estimate is made using the whole imaging screen as a unit, the load of the image processing circuit 62 can be low, so that high-speed processing and the small-size image processing circuit 62 are possible.

Here, the two examples described above are extreme cases, and it is also obviously possible to set an intermediate region as the narrow-band light intensity derivation region. For example, it is possible to divide the imaging screen into several regions, make an estimate for each of these regions. Such processing can simultaneously achieve color reproducibility, the processing speed, and the size reduction of circuits.

Narrowing down the regions to make estimates by removing the regions to make no estimates is also advantageous. For example, a proper correction can be made by removing regions having blown-out highlights and regions having blocked-up shadows, and regions having extremely weak or strong incident light amount in the dynamic range of the image sensor 58, i.e., regions located in the vicinity of the upper limit and lower limit of the dynamic range of the image sensor 58 (FIG. 11). Moreover, when an anticipated ratio of the color sensitivity regions 1, 2, and 3 of the narrow-band light spectral intensity information (wavelength λ, light receiving intensity P) of the observation target 90 is known, it is possible to automatically extract an image region having a ratio close to the above ratio alone, and make an image correction in the region alone. It is also possible for an operator to specify a region for which an image correction is to be made through the input section 70. As above, it is possible to reduce the load of the image processing circuit 62, and perform high-speed image processing and yet improve the color reproducibility of the desired observation target 90 by specifying the region to improve color reproducibility and making an image correction using estimation work in the part alone.

When the image region to estimate the wavelength lacking region spectral intensity information changes as above, the basic configuration of the observation apparatus described above does not change, but the method of extracting the narrow-band light spectral intensity information (wavelength λ, light receiving intensity P) by the image processing circuit 62 differs. Regarding the narrow-band light spectral intensity information, the calculation of the light receiving intensity P for the wavelength information λ is described next.

<Calculation of Narrow-Band Light Spectral Intensity Information and Light Receiving Intensity P for Wavelength λ>

Basically, it is preferable for the light receiving intensity P to take an average value in the image region to be estimated. That is, when an estimate is made regarding four pixels of 2×2 that is the minimum unit as shown in FIG. 9 for the image sensor 58 having the Bayer array, detection values remain as $P_{1, detect}$ and $P_{3, detect}$ regarding the color sensitivity region 1 (B region) and the color sensitivity region 3 (R region). On the other hand, regarding the color sensitivity region 2 (G region), two pixels are present, so that $P_{2, detect}$ can be found by taking an average of these pixels. That is, $P_{2, detect} = (P_{2a, detect} + P_{2b, detect})/2$ can be found wherein $P_{2a}$ and $P_{2b}$ are received light intensities detected by the two G pixels.

Similarly, when an estimate and an image correction are collectively made for the whole imaging screen as shown in FIG. 10, it is only necessary to calculate, for each color sensitivity region, an average of the received light intensities received by the respective pixels of the color sensitivity region 1, the color sensitivity region 2, and the color sensitivity region 3 in the whole imaging screen, thereby finding received light intensities $P_{1, detect}$, $P_{2, detect}$ and $P_{3, detect}$.

The received light intensities can be found in a basically similar manner when the aforementioned whole imaging screen is divided into several intermediate regions (e.g. regions of 10×10 pixels shown in FIG. 10) and an average value is found for each of the intermediate regions.

It is also possible to use methods other than the method of finding the average value as a method of the representative value. As an example, it is also possible to use a value of the highest frequency in a predetermined region as a representative value. That is, the light receiving intensity having the greatest number of pixels can be used as the representative value in a histogram in which the light receiving intensity of each pixel is indicated on the horizontal axis and the number of pixels is indicated on the vertical axis. According to the method, the light receiving intensity of the region having the greatest number of pixels, i.e., the largest region in the predetermined region of the whole imaging screen can be used as a representative value, so that the color reproducibility of the largest region can be improved.

As another example, the value of the pixel having the highest light receiving intensity in a particular color sensitivity region can be the representative value. For example, in the case of an endoscope apparatus, the color reproducibility of the red region is important because the internal surface of a living body that is the observation target 90 is mostly red. Thus, if the value of the pixel having the highest light receiving intensity in the color sensitivity region 3 (R pixel) is used as the representative value, the color reproducibility of the red observation target 90 can be further improved (FIG. 11). Although cell lines to image the pixels do not correspond to lines indicating the incident light amount and the boundaries of the color regions for convenience in FIG. 11, it goes without saying that the lines to set such boundaries also correspond to the aforementioned minimum unit in actual scenes.

It is also possible to find the representative value by combining the above. For example, it is possible to find a representative value by extracting pixels having the highest light receiving intensity in a particular color sensitivity region such as the red region and finding an average value of these pixels. According to such a method, it is possible to improve the color reproducibility of the red-tinged observation target 90 including red-tinged regions other than bright red regions.

[Operation]

Next, the operation in the present embodiment is described.

As shown in FIG. 1, the semiconductor lasers 22A, 22B, and 22C are connected to the light source control circuit 30 across the drive circuits 26A, 26B, and 26C. The light source control circuit 30 outputs control signals to the drive circuits 26A, 26B, and 26C through the control signal lines 28 connected to the drive circuits 26A, 26B, and 26C in accordance with an input from the outside that is not shown and information regarding the image processing circuit 62. The drive circuits 26A, 26B, and 26C supply, to the semiconductor lasers 22A, 22B, and 22C, electric power corresponding to the control signals from the light source control circuit 30, respectively. The semiconductor lasers 22A, 22B, and 22C use the obtained electric power to emit laser lights having specific wavelengths in the light amounts and timings required by the light source control circuit 30. The laser lights enter the light combiner 34 through the optical fibers 32A, 32B, and 32C connected to the semiconductor lasers 22A, 22B, and 22C. The laser lights having three different wavelengths that have entered the light combiner 34 are optically coupled together, and enter the optical fiber 46. The laser lights having the three wavelengths that have entered the optical fiber 46 propagate through the optical fiber 46, and enter the light exit 48 provided at the end of the optical fiber. The light exit 48 is configured as shown in FIG. 5 by way of example. The laser lights that have entered the light exit 48 become illumination lights that are diffused lights through the operation described in the section <Light exit>, and are applied to the surface of the internal space 92 of the observation target 90.

In accordance with the characteristics required for the illumination lights, the light source control circuit 30 can set the light amount ratio and timings of the light emission of the respective semiconductor lasers 22A, 22B, and 22C. For example, red, green, and blue can be lighted in the order. It is also possible to emit a particular combination of lights by particular timing.

The illumination lights sent out from the light exit 48 are the blue laser light, the green laser light, and the red laser light that are three narrow-band lights in terms of wavelength. The distribution of the illumination lights is fully diffused, and the illumination lights are diffused lights fully lowered in coherency. Such an illumination light is applied to the observation target 90, and becomes a reflected/scattered light corresponding to the spectral reflection factor of the observation target 90. A component of the reflected/scattered light that travels to the image sensor 58 provided at the distal end 18 of the insertion portion 14 enters the image sensor 58, and is detected as an image signal. The image sensor 58 has an R light sensitivity region, a G light sensitivity region, and a B light sensitivity region that are three wavelength sensitivity bands shown in FIG. 6. The relation among the light sensitivity regions of the image sensor 58 and the wavelengths of the three narrow-band lights is as described above. Thus, the red laser light from the semiconductor laser 22C enters the light detection element corresponding to the R light sensitivity region after reflected in accordance with the spectral reflection factor for the red light of the observation target 90. Similarly, the green laser light from the semiconductor laser 22B enters the light detection element corresponding to the G light sensitivity region, and the blue laser light from the semiconductor laser 22A enters the light detection element corresponding to the B light sensitivity region. That is, one narrow-band light enters one of the R light detection element, the G light detection element, and the B light detection element. In the present embodiment, the intensity ratio of the three narrow-band lights, which are the illumination lights sent out from the semiconductor lasers 22A, 22B, and 22C and sent out from the light exit 48, is a substantially equal intensity ratio as shown in FIG. 7. Therefore, when the spectral reflection factor of the observation target 90 is flat, the amount of the light that enters each light detection element is designed to show substantially equal intensity. When the spectral reflection factor is not flat, the amount of the light that enters each light detection element is received by each light detection element at an intensity ratio that conforms to the spectral reflection factor at the wavelengths of the narrow-band lights $\lambda_1$ to $\lambda_3$ that enter the respective light detection element.

The reflected/scattered light of the illumination light that has entered the image sensor 58 is converted into an imaging signal by the image sensor 58 and an unshown electric circuit, and transmitted to the image processing circuit 62 through the signal line 60. In the image processing circuit 62 that has received the imaging signal, the wavelength lacking region spectral intensity information estimator 64 estimates the spectral intensity of the wavelength lacking regions for each unit to estimate the spectral intensity of the wavelength lacking regions (FIG. 7). In the present embodiment, the image sensor 58 having the Bayer array is assumed, and the unit to estimate the spectral intensity is the minimum unit of 2×2 pixels.

First, the image processing circuit 62 calculates the narrow-band light spectral intensity information ($\lambda$, P) for each of the aforementioned minimum unit of 2×2 pixels. In the present embodiment, the intensities of the three laser lights sent out from the light exit 48 are equal to one another. That is, in the spectra of the illumination lights shown in the uppermost section in FIG. 7, the peak intensities at the peak wavelengths $\lambda_1$, $\lambda_2$, and $\lambda_3$ of the respective laser lights are $I_1=I_2=I_3=I$.

The illumination light sent out from the light exit 48 is reflected/scattered in accordance with the spectral reflection factor that is a wavelength-to-wavelength reflection factor of the observation target 90, and partly enters the image sensor 58. If the amount of the light that has entered the minimum unit of the image sensor 58 to estimate the spectral intensity is $P_1$ in the color sensitivity region 1 (B pixel) and $P_3$ in the color sensitivity region 3 (R pixel), narrow-band light intensity coordinates are ($\lambda_1$, $P_1$) and ($\lambda_3$, $P_3$), respectively. In the color sensitivity region 2 (G pixel) having two pixels, narrow-band light intensity coordinates are ($\lambda_2$, $P_2$) by the use of $P_2$ that is found when $P_2=(P_{2a}+P_{2b})/2$ wherein $P_{2a}$ is the intensity of the light that has entered the first G pixel, and $P_{2b}$ is the intensity of the light that has entered the second G pixel.

Here, $P_1$, $P_2$, and $P_3$ in the narrow-band light spectral intensity information ($\lambda$, P) need to be in the ratio of the light amounts that enter the respective color sensitivity regions of light receiving elements when a light of a constant intensity enters. Thus, if the intensities of the three laser lights are $I_1$, $I_2$, and $I_3$, P of the narrow-band light spectral intensity information ($\lambda$, P) should be $P_1/I_1$, $P_2/I_2$, and $P_3/I_3$ when the light amounts that have entered light receiving elements are $P_1$, $P_2$, and $P_3$, respectively. However, such a calculation is unnecessary because $I_1=I_2=I_3=I$ in the present embodiment.

As described above, the image processing circuit 62 derives the narrow-band light spectral intensity information as ($\lambda_1$, $P_1$), ($\lambda_2$, $P_2$), and ($\lambda_3$, $P_3$) by a narrow-band light spectral intensity information generation section that estimates the narrow-band light spectral intensity information ($\lambda$, P).

The image processing circuit then estimates the spectral intensity information of the wavelength lacking regions by the wavelength lacking region spectral intensity information estimator 64. The wavelength lacking region spectral intensity information estimator 64 uses a functional approximation technique to estimate the spectral intensity information for the first wavelength lacking region from the information regarding three coordinates that are the narrow-band light spectral intensity information. The functional approximation technique is used in various technical fields. Any technique that interpolates between coordinates may be used. In the present embodiment, as shown in FIG. 7, an estimate is only made for the first wavelength lacking region that is the region between two adjacent laser lights among the wavelength lacking regions.

On the basis of the first wavelength lacking region spectral intensity information estimated by the wavelength lacking region spectral intensity information estimator 64, the wavelength lacking region correction processor 66 makes an image correction, and performs image correction processing such that the image will be closer to the image obtained by the use of the illumination light having no wavelength lacking regions (a broadband light having a wavelength band spreading in the whole wavelength region that can be detected by the image sensor 58).

In the color sensitivity region that is the wavelength range detectable by each color sensitivity region of the image sensor 58, the wavelength lacking region correction processor 66 estimates, on the basis of the first wavelength lacking region spectral intensity information, the light intensity information $P_{1,\ estimate}$ to be received by each color sensitivity region of the image sensor 58 when the same observation target 90 is observed by use of the illumination light having no wavelength lacking regions. That is, a correction value to correct $P_{1,\ detect}$ that is the light intensity information that has actually entered the color sensitivity region 1 of the image sensor 58 by the illumination light having wavelength lacking regions to the light intensity information $P_{1,\ estimate}$ is found.

The wavelength lacking region correction processor 66 integrates the estimated first wavelength lacking region spectral intensity information regarding a region located in the color sensitivity region 1 and between the wavelength of the semiconductor laser 22A and the wavelength of the semiconductor laser 22B, and finds its area (FIG. 8). The wavelength lacking region correction processor 66 then finds the height of a hypothetical rectangle that has the same area as the found area. The height is $P_{1,\ estimate}$.

$P_{2,\ estimate}$ and $P_{3,\ estimate}$ can also be found for the color sensitivity regions 2 and 3 by similar processing.

Although the estimation work is supposed to be done for each Bayer array that is the minimum unit for each image observed by the observation apparatus in the present embodiment, the present invention is not limited to this.

For example, it is also appropriate that processing be performed so that a correction coefficient $P_{1,\ estimate}/P_{1,\ detect}$ is found after $P_{1,\ estimate}$ is found for the image obtained by certain timing, and for the image obtained next, the correction coefficient is multiplied by the light intensity information before correction. That is, $P_{1',\ estimate} = P_{1',\ detect} \times P_{1,\ estimate}/P_{1,\ detect}$ can be found wherein $P_{1',\ detect}$ is the light intensity information of the color sensitivity region 1 in the image obtained next. In this way, it is possible to reduce the load of the image processing circuit 62, and perform high-speed image display.

Although the estimated wavelength lacking region spectral intensity information is integrated to find the post-correction light intensity information $P_{,\ estimate}$ in the example shown in the present embodiment, the present invention is not limited to this. For example, an average value of light intensities may be found in the wavelength range of the wavelength lacking region spectral intensity information effective in each color sensitivity region. According to the method, $P_{,\ estimate}$ can be more easily found than according to the method that uses integration. Moreover, an average of the minimum value and the maximum value of the same wavelength range may be found. According to this method, $P_{,\ estimate}$ can be more easily found.

The image processing circuit 62 transmits the image signal corrected on the basis of $P_{,\ estimate}$ found as above to the display 20 as the corrected light receiving amount information PP.

Although the wavelength lacking region spectral intensity information is estimated to only correct the first wavelength lacking regions that are the wavelength lacking regions between the narrow-band lights in the example shown in the present embodiment, the present invention is not limited to this. For the second wavelength lacking regions, the wavelength lacking region spectral intensity information can be estimated by extrapolation to find post-correction light intensity information $P_{,\ estimate}$ by the aforementioned method. In this way, it is possible to estimate the wavelength lacking region spectral intensity information in a wider wavelength range for use in $P_{,\ estimate}$. This is advantageous, for example, when narrow-band lights concentrate in some wavelength regions such as the green to red regions whether the number of the narrow-band lights is two or three or more.

A correction that takes the sensitivity characteristics of the image sensor 58 into consideration may be further made. The image sensor 58 has specific properties depending on the difference of its materials, and the image sensor 58 comprising a silicon semiconductor has significantly low detection sensitivity in a wavelength region of 400 nm or less. In contrast, the image sensor 58 has high detection sensitivity on the long wavelength side, and also has satisfactory detection sensitivity in a near-infrared region. Moreover, to determine the width of the color sensitivity region, the image sensor 58 has a filter having wavelength characteristics shown in the upper section in FIG. 6. Further, an unshown infrared cutoff filter, and various other filters are used together for each purpose. Such filter characteristics affect the spectra of the illumination lights and/or the intensity of the light receiving intensity P of the narrow-band light spectral intensity information ($\lambda$, P) in FIG. 7. The characteristics of the image sensor 58 and the wavelength characteristics of the filters are known in advance, so that to correct these characteristics, $P_{,\ detect,\ real}$ that enters the image sensor 58 may be estimated from the actually detected light intensity $P_{,\ detect}$. By performing such processing, it is possible to estimate more accurate spectral intensity information for the wavelength lacking regions, and improve color reproducibility.

[Functions—Advantageous Effects]

As described above, according to the configuration in the present embodiment, it is possible to improve the color reproducibility of the observation apparatus that uses the illumination light having wavelength lacking regions so that the image will be closer to the image obtained by the observation apparatus that uses the illumination light having no wavelength lacking regions. Especially in the observation apparatus that uses the laser light having a particularly narrow wavelength width for the illumination light as the narrow-band light and in which most of the region that can be detected by the image sensor 58 comprises the wavelength lacking regions, it is possible to obtain an image closer to the image obtained by use of the illumination light having no wavelength lacking regions by adding a function to the image processing circuit 62.

Furthermore, as described above, it is possible to obtain an image having high color reproducibility at a speed compatible with a high frame rate by performing collective the wavelength lacking region correction processing for the whole imaging screen.

It is also possible to obtain an image having high color reproducibility in the whole imaging screen by performing the wavelength lacking region correction processing for each minimum unit of the image sensor 58.

Moreover, various combinations and modifications can be made without departing from the above description, and it is possible to provide an observation apparatus that has a speed, a circuit scale, and a size suited to the purpose and that is capable of obtaining an image that is high in color reproducibility.

Modification of First Embodiment

Next, a modification of the first embodiment is described with reference to FIG. 12.

The present modification is different from the first embodiment in the function of the wavelength lacking region spectral intensity information estimator 64 of the image processing circuit 62. In the method shown in the first embodiment, as shown in FIG. 7, a hypothetical curve that smoothly and continuously connects the coordinates of three points is calculated by interpolation in accordance with the smoothing technique using the functional approximation regarding the narrow-band light spectral intensity information (wavelength λ, light receiving intensity P) corresponding to three narrow-band lights. The present modification is different from the first embodiment in that the wavelength lacking region spectral intensity information estimator 64 estimates the wavelength lacking region spectral intensity information to obtain discontinuous straight lines as shown in FIG. 12.

Figure 12:
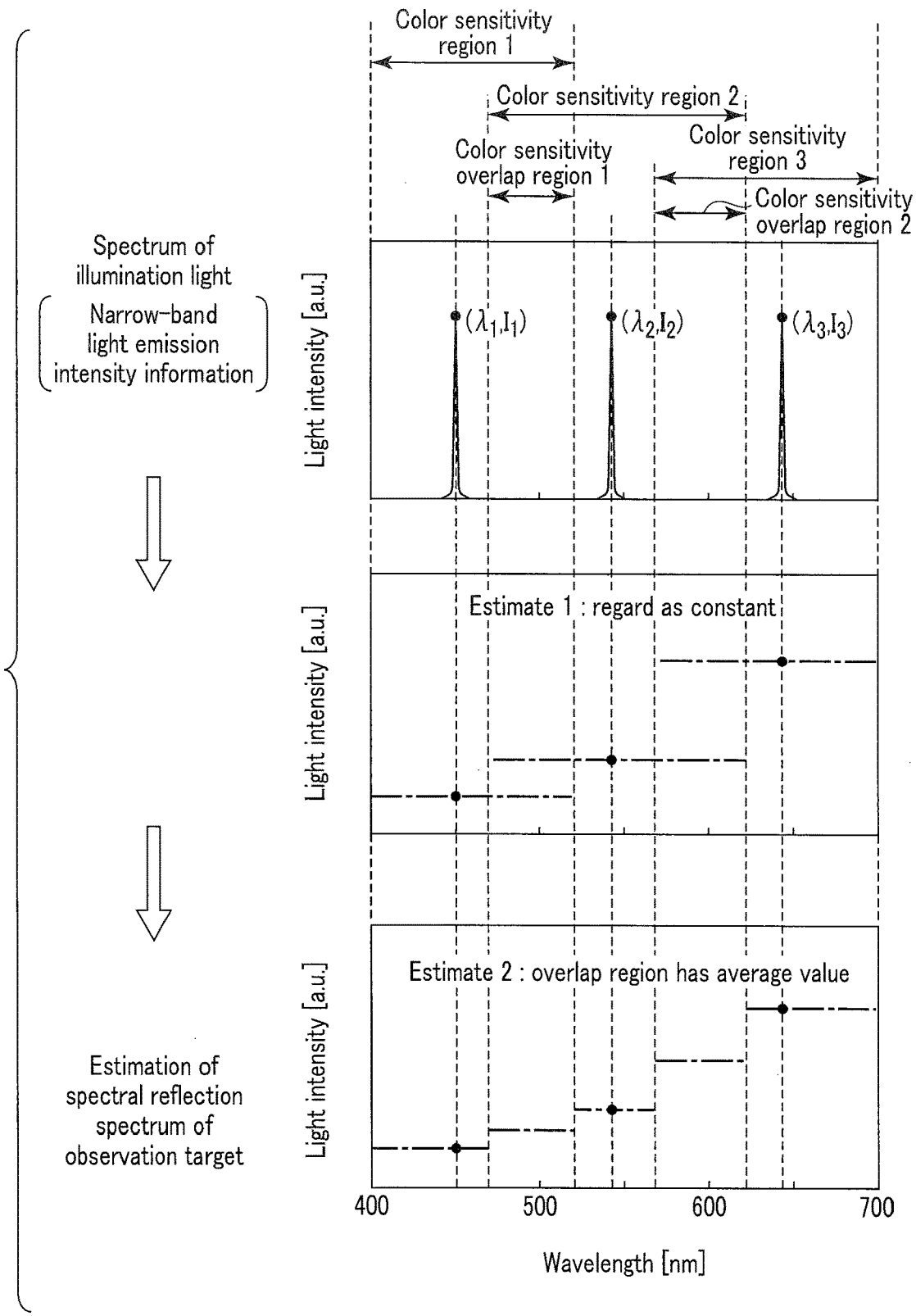
FIG. 12 shows estimation examples of the narrow-band light emission information and the first wavelength lacking region spectral intensity information in a modification of the first embodiment.

A modification shown in the middle section of FIG. 12 shows an example of estimation (Estimate 1) on the assumption that the light receiving intensity received by the light detection element corresponding to each color sensitivity region of the image sensor 58 is constant light intensity in the whole wavelength region. For example, in the case of the light receiving intensity P at the point of the wavelength $\lambda_1$, the spectral intensity of the wavelength lacking region is estimated on the assumption that the light of constant intensity is applied to the whole wavelength region where the color sensitivity region 1 receives the light. In this configuration, spectral intensity information for the wavelength lacking region can be estimated by an extremely simple configuration. Moreover, such estimation allows correcting the filter characteristics of the image sensor 58 and the received light sensitivity characteristics of the image sensor 58 that cannot be corrected using information on one point, and estimate spectral information for incident light when the illumination light having no wavelength lacking regions is reflected/scattered by the observation target 90 and enters the image sensor 58.

Furthermore, the color sensitivity region of the image sensor 58 shown in the first embodiment overlaps the adjacent color sensitivity region. Thus, in "Estimate 1", different spectral intensity information is estimated for each of the color sensitivity regions on both sides of each of the sensitivity overlap regions 1 and 2. In contrast, in the example of "Estimate 2" shown in the lower section of FIG. 12, the wavelength lacking region spectral intensity information is estimated by the average value of the received light intensities P received by the light detection elements corresponding to two color sensitivity regions regarding the sensitivity overlap region of the adjacent color sensitivity regions in the wavelength lacking region. Consequently, as compared to the example shown in "Estimate 1", it is possible to improve color reproducibility without considerably deteriorating the calculation speed to calculate an estimate so that the image will be closer to the image obtained by use of the illumination light having no wavelength lacking regions.

In the configuration according to the present modification, the estimation method of the wavelength lacking region spectral intensity information estimator 64 in the image processing circuit 62 is only changed, so that as other components, the various components shown in the first embodiment can be used. Such a modification can be achieved by only changing the software of the image processing circuit 62, and it is therefore also appropriate that the modification be only used in the timing that gives priority to the calculation speed over color reproducibility and that the smoothing technique based on the functional approximation providing smoothness and continuation shown in the first embodiment can be used in other timings.

Second Embodiment

Next, the second embodiment of the present invention is described with reference to FIG. 13 to FIG. 15.

The same parts in the second embodiment as those in the first embodiment are not described, and different parts are only described.

In the example shown in the first embodiment, the number of the color sensitivity regions and the number of the narrow-band lights are equal and three, and one narrow-band light 1, 2, 3 is disposed for each of the three color sensitivity regions 1, 2, and 3. The present embodiment is different from the first embodiment in that four narrow-band lights 1, 2, 3-1, and 3-2 are disposed for three color sensitivity regions.

[Configuration]

Figure 13:
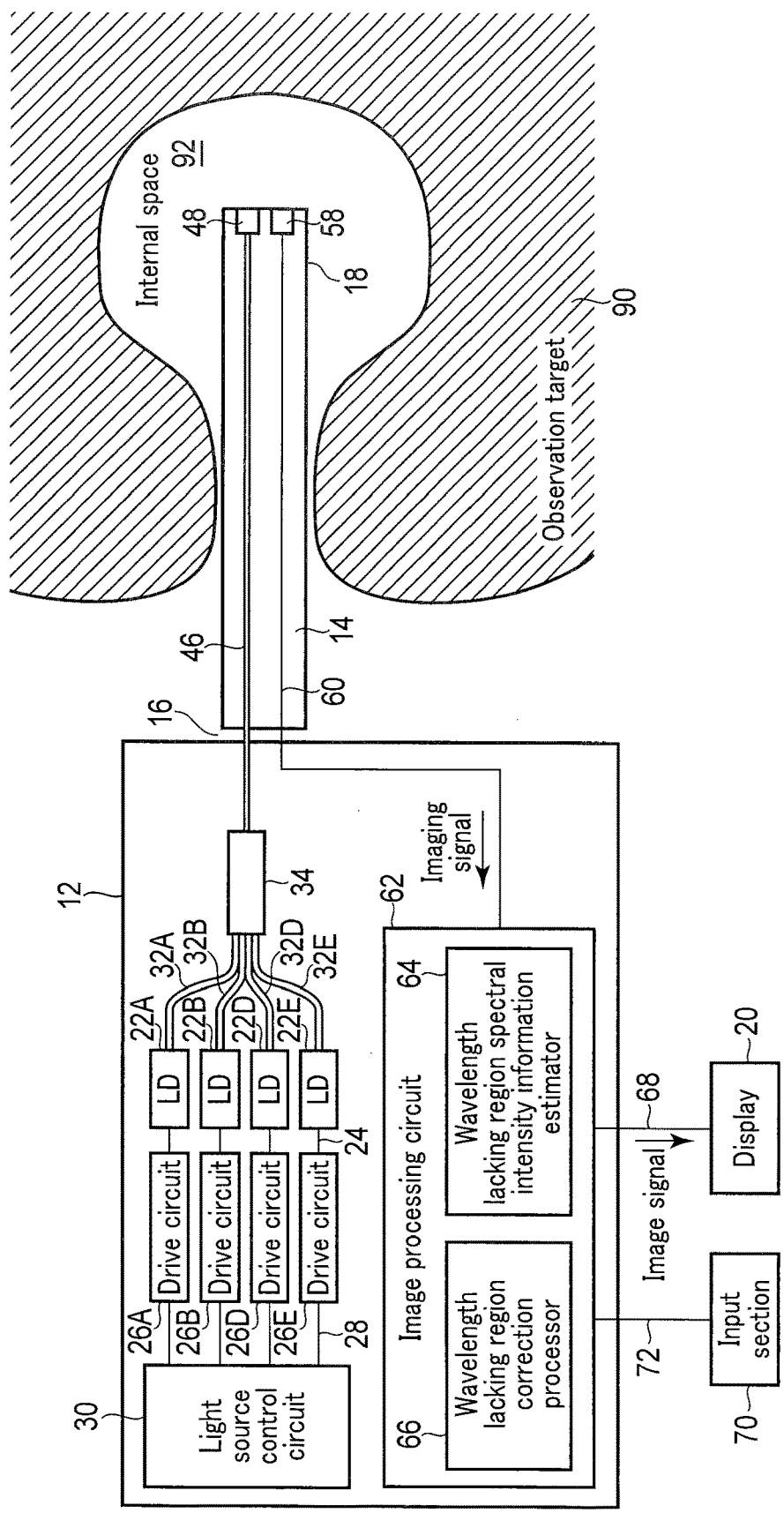
FIG. 13 schematically shows the observation apparatus in a second embodiment.

The observation apparatus in the present embodiment is shown in FIG. 13.

In the present embodiment, the light source portion that radiates four narrow-band lights is used, as described above. Thus, the body portion 12 includes four semiconductor lasers 22A, 22B, 22D, and 22E, drive circuits 26A, 26B, and 26D, and 26E that are combined with the semiconductor lasers, and four optical fibers 32A, 32B, 32D, and 32E that respectively guide laser lights sent out from the semiconductor lasers 22A, 22B, 22D, and 22E. The light source control circuit 30 is electrically connected to the drive circuits 26A, 26B, and 26D, and 26E by the control signal lines 28, and can freely control the semiconductor lasers 22A, 22B, 22D, and 22E through the drive circuits 26A, 26B, and 26D, and 26E. The semiconductor lasers 22A, 22B, 22D, and 22E are coupled to the light combiner 34 by the optical fibers 32A, 32B, 32D, and 32E, respectively. The light combiner 34 combines the laser lights guided by the four optical fibers 32A, 32B, 32D, and 32E, and outputs the laser lights to the optical fiber 46.

The four lasers used in the present embodiment are as follows:

The semiconductor laser 22A is a multimode semiconductor laser that radiates a blue laser light that is the narrow-band light 1 having a wavelength of approximately 450 nm.

The semiconductor laser 22B is a multimode semiconductor laser that radiates a green laser light that is the narrow-band light 2 having a wavelength of approximately 540 nm.

The semiconductor laser 22D is a multimode semiconductor laser that radiates a red laser light that is the narrow-band light 3-1 having a wavelength of approximately 630 nm.

The semiconductor laser 22E is a multimode semiconductor laser that radiates a red laser light that is the narrow-band light 3-2 having a wavelength of approximately 680 nm.

That is, the semiconductor lasers 22A and 22B are the same multimode semiconductor lasers as those in the first embodiment. The semiconductor laser 22D is a multimode semiconductor laser having a peak wavelength of 630 nm that radiates a light having a peak wavelength 10 nm shorter than the semiconductor laser 22C in the first embodiment. The semiconductor laser 22E is a multimode semiconductor laser having a peak wavelength of 680 nm. Both the narrow-band lights 3-1 and 3-2 respectively sent out by the semiconductor lasers 22D and 22E are only included in the color sensitivity region 3, as shown in FIG. 14.

[Operation]

The basic operation is similar to that in the first embodiment, and the operation of the image processing circuit 62 is slightly different.

Under the instruction from the light source control circuit 30, each of the semiconductor lasers 22A, 22B, 22D, and 22E radiates the laser light having a predetermined wavelength and light amount. The narrow-band light that is the laser light sent out from each of the semiconductor lasers 22A, 22B, 22D, and 22E is combined by the light combiner 34, guided by the optical fiber 46, and applied to the surface of the internal space 92 of the observation target 90 from the light exit 48 as an illumination light.

The semiconductor lasers 22A, 22B, 22D, and 22E can freely emit lights by the light source control circuit 30, but are controlled so that all the semiconductor lasers are continuously turned on in a basic emission mode in the present embodiment. That is, the semiconductor lasers 22A, 22B, 22D, and 22E are adjusted to substantially equal light intensity and continuously emit light as shown in the upper section in FIG. 15. That is, the semiconductor lasers 22A, 22B, 22D, and 22E are configured so that $I_1=I_2=I_4=I_5=I$.

Part of the illumination light reflected/scattered by the observation target 90 enters the image sensor 58, and is transmitted to the image processing circuit 62 as an imaging signal.

In the present embodiment as well, the image sensor 58 having the Bayer array is assumed, and the unit to estimate the spectral intensity is the minimum unit of 2×2 pixels. In this instance, the lights that enter the pixels in the color sensitivity region 1 and the pixels in the color sensitivity region 2 of the image sensor 58 are the blue laser light and the green laser light, respectively, and are similar to those in the first embodiment. That is, the color sensitivity region 1 and the color sensitivity region 2 are single narrow-band light color sensitivity regions. In contrast, the lights that enter the pixels in the color sensitivity region 3 are two narrow-band lights: the red laser light (630 nm), and the red laser light (680 nm). The light detection element corresponding to the color sensitivity region 3 of the image sensor 58 receives the red laser lights having these two wavelengths with no distinction, and outputs the corresponding imaging signal to the image processing circuit 62. That is, the image processing circuit 62 receives the red laser light (630 nm) and the red laser light (680 nm) sent out from the semiconductor laser 22D and 22E as information from the pixels in the color sensitivity region 3 that is one color sensitivity region. In other words, the color sensitivity region 3 is a multiple narrow-band light color sensitivity region that receives two narrow-band lights: the narrow-band light 3-1 and the narrow-band light 3-2.

The image processing circuit 62 derives the narrow-band light spectral intensity information ($\lambda$, P) on the basis of information regarding the three color sensitivity regions 1, 2, and 3, as in the first embodiment. That is, in a certain unit, light intensities output from the light detection elements corresponding to the color sensitivity regions 1, 2, and 3 are $P_1$, $P_{2a}$, $P_{2b}$, and $P_3$, respectively. In this instance, the narrow-band light spectral intensity information for the color sensitivity region 1 (B pixel) is ($\lambda_1$, $P_1$), the narrow-band light spectral intensity information for the color sensitivity region 2 (G pixel) is ($\lambda_2$, $P_2=(P_{2a}+P_{2b})/2$), which are not different from those in the first embodiment. Meanwhile, the narrow-band light spectral intensity information of the color sensitivity region 3 (R pixel) is (($\lambda_4+\lambda_5$)/2, $P_3$).

That is, the light that enters the pixels in the color sensitivity region 3 is a mixed light of the narrow-band light 3-1 having the wavelength $\lambda_4$ and the narrow-band light 3-2 having the wavelength $\lambda_5$. However, the light detection element corresponding to the color sensitivity region 3 cannot discriminately detect the light of $\lambda_4$ and the light of $\lambda_5$, and therefore derives the narrow-band light spectral intensity information as (($\lambda_4+\lambda_5$)/2, $P_3$) on the hypothesis that a narrow-band light of ($\lambda_4+\lambda_5$)/2 has entered. Here, the intensity $I_4$ of the narrow-band light of $\lambda_4$ is equal to the intensity $I_5$ of the narrow-band light of $\lambda_5$, so that the hypothetical wavelength ($\lambda_4+\lambda_5$)/2 is found as a simple arithmetic mean. However, in the case of $I_4 \neq I_5$, these need to be taken into consideration so that the narrow-band light spectral intensity information may be (($I_4 \times \lambda_4 + I_5 \times \lambda_5)/(I_4+I_5)$, $P_3$). Thus, it is necessary for the multiple narrow-band light color sensitivity region 3 to have the narrow-band light spectral intensity information (($I_4 \times \lambda_4 + I_5 \times \lambda_5)/(I_4+I_5)$, $P_3$).

The narrow-band light spectral intensity information is found as above, so that the narrow-band light spectral intensity information can be found even if one color sensitivity region includes more than one narrow-band light.

The operation after the derivation of the narrow-band light spectral intensity information in the present embodiment is similar that in the first embodiment.

In the example shown in the present embodiment, two narrow-band lights are included in one color sensitivity region, but are not included in the sensitivity overlap region where two color sensitivity regions overlap. However, the present invention is not limited to this. Hypothetical wavelengths can also be calculated when the narrow-band light is present in a region that is included in more than one color sensitivity region and in which the color sensitivity regions overlap. In this instance, the narrow-band light that is present in the region where the color sensitivity regions overlap needs to be used in the calculation of the hypothetical wavelengths of two color sensitivity regions.

Figure 14:
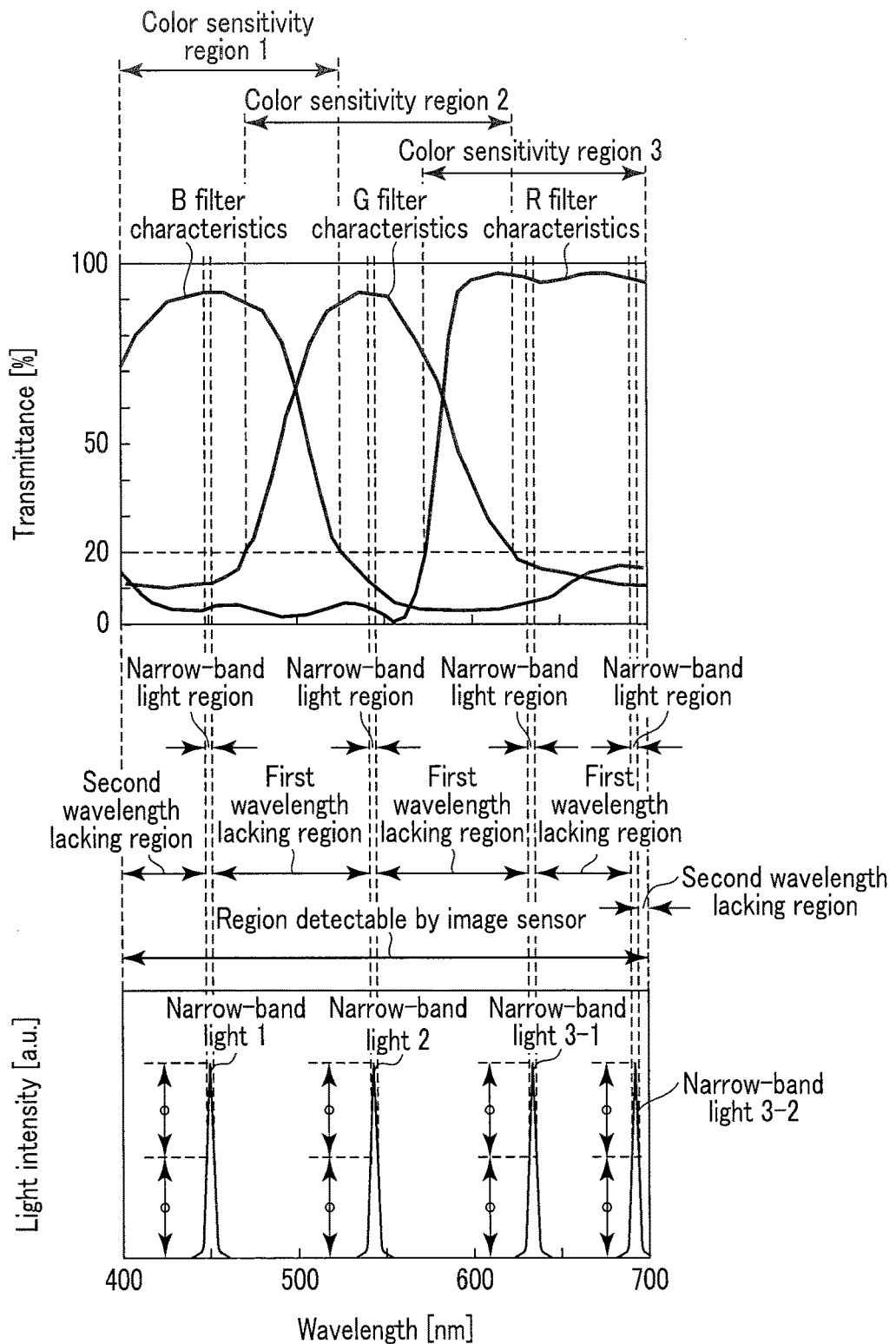
FIG. 14 shows the relation between the color sensitivity regions, the narrow-band light regions, and the wavelength lacking regions in the second embodiment.
Figure 15:
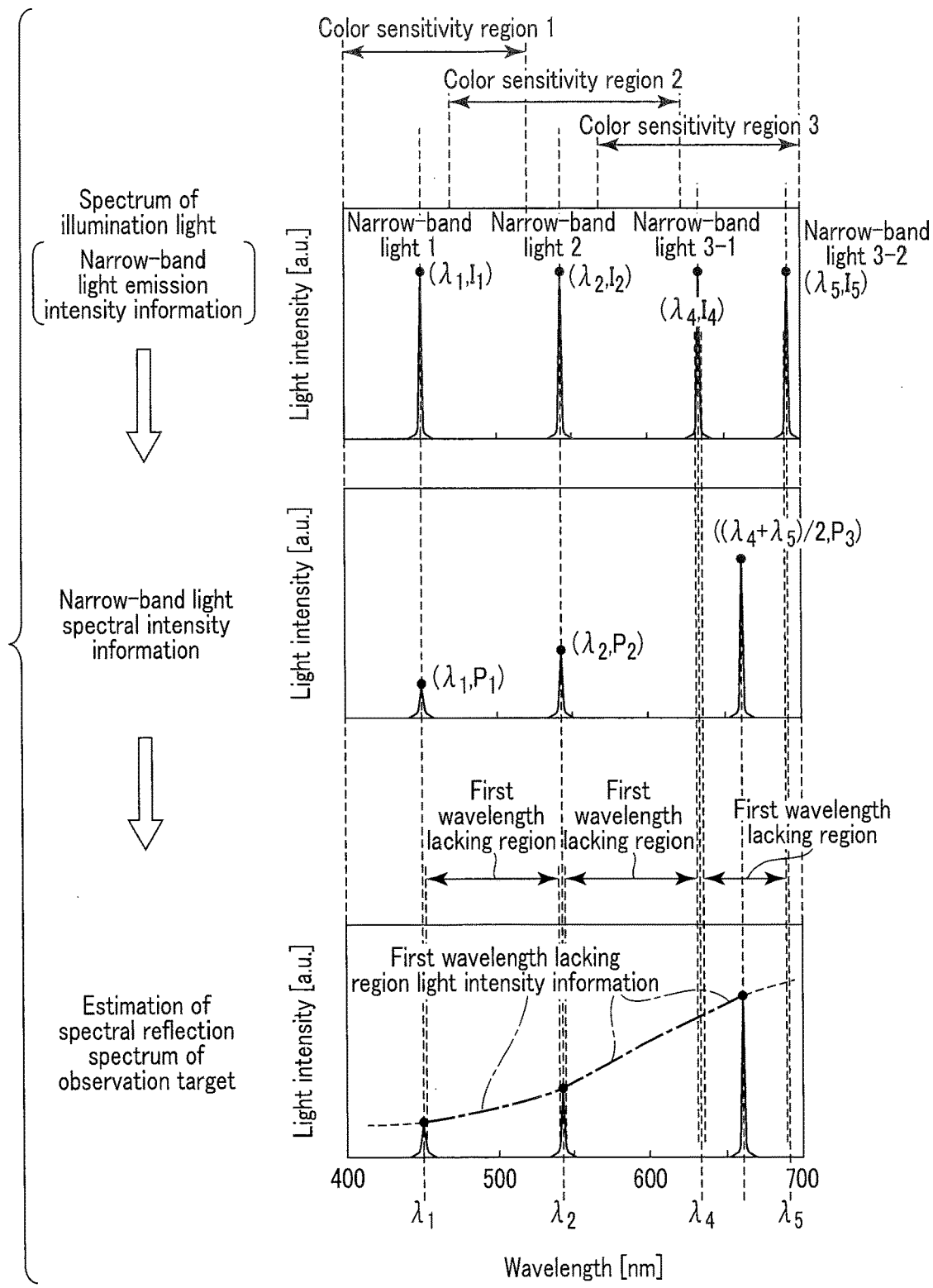
FIG. 15 shows the narrow-band light emission information, the narrow-band light spectral information, and the estimated first wavelength lacking region spectral intensity information in the second embodiment.

In the sensitivity overlap region of two color sensitivity regions, filter transmission characteristics may not be high enough, as shown in FIG. 14 and others. In this case, it is preferable to calculate the hypothetical wavelength including the filter transmission characteristics.

[Functions—Advantageous Effects]

According to the configuration described above, even if one color sensitivity region is configured to include more than one narrow-band light, the narrow-band light spectral intensity information can be found while the respective narrow-band lights are sent out simultaneously, for example, continuously, and various wavelength lacking region spectral intensity information shown in the first embodiment can be estimated. As a result, even when the illumination light having wavelength lacking regions is used, it is possible to perform image processing such that the image will be closer to the image obtained by the use of the illumination light having no wavelength lacking regions.

According to the configuration in the present embodiment, no special additional components and additional processing are needed, and the present function can be obtained only by the change of, for example, a program for narrow-band light intensity information derivation. Therefore, for example, it is easy to switch and use suitably to, for example, the observation target 90 and observation purposes; the method according to the first embodiment is used when the semiconductor lasers 22A, 22B, and 22D according to the present embodiment alone are turned on, and the method according to the second embodiment is used when all the semiconductor lasers 22A, 22B, 22D, and 22E including the semiconductor laser 22E are turned on.

Third Embodiment

Next, the third embodiment is described with reference to FIG. 16 and FIG. 17.

The same parts as those in the first and second embodiments are not described, and different parts are only described.

[Configuration—Operation]

In the present embodiment, as shown in FIG. 13, the light source control circuit 30 is electrically connected to the drive circuits 26A, 26B, and 26D, and 26E so that the semiconductor lasers 22A, 22B, 22D, and 22E can be turned on/off with desired brightness and by desired timing. The wavelength relation between the image sensor 58 and the semiconductor lasers 22A, 22B, 22D, and 22E in the present embodiment is similar to that in the second embodiment shown in FIG. 14. That is, the four multimode semiconductor lasers 22A, 22B, 22D, and 22E have the same emission wavelengths as those in the second embodiment, are configured so that the blue laser light of the semiconductor laser 22A is only included in the color sensitivity region 1, the green laser light of the semiconductor laser 22B is only included in the color sensitivity region 2, and the red laser light (630 nm) of the semiconductor laser 22D and the red laser light (680 nm) of the semiconductor laser 22E are only included in the color sensitivity region 3. The color sensitivity region 1 and the color sensitivity region 2 are single narrow-band light color sensitivity regions. The color sensitivity region 3 is a multiple narrow-band light color sensitivity region.

The present embodiment is different from the second embodiment in that the timing of the light emission of the semiconductor laser 22D is different from the timing of the light emission of the semiconductor laser 22E. That is, three semiconductor lasers and four semiconductor lasers simultaneously and continuously emit lights in the examples shown in the first embodiment and the second embodiment, respectively. However, the difference in the third embodiment is that each of the semiconductor lasers 22A, 22B, 22D, and 22E is turned on/off for each frame timing by which the image sensor 58 performs an imaging operation for one image. The relation between each of the semiconductor lasers 22A, 22B, 22D, and 22E and the frame timing in the present embodiment is shown in FIG. 16. In this example, the light source control circuit 30 drives the semiconductor lasers 22A, 22B, 22D, and 22E in accordance with the frame timing of the image sensor 58 to alternately repeat a frame (even-numbered frame in the drawing) in which the semiconductor lasers 22A and 22D are turned on and the semiconductor lasers 22B and 22E are turned off, and a frame (odd-numbered frame in the drawing) in which the semiconductor lasers 22B and 22E are turned on and the semiconductor lasers 22A and 22D are turned off. In this instance, information on the frame timing of the image sensor 58 is transmitted to the light source control circuit 30 by unshown frame timing information transmitting means, and the light source control circuit 30 turns on/off each of the semiconductor lasers 22A, 22B, 22D, and 22E by proper timing in accordance with the frame timing information.

When such light emission control is performed, the image signals transmitted from the image sensor 58 are as follows: In the even frame, the imaging signal by the blue laser in the color sensitivity region 1 and the imaging signal by the red laser (630 nm) in the color sensitivity region 3 are output, and a deep-black imaging signal is output because there is no illumination light of the corresponding wavelength region in the color sensitivity region 2. Similarly, in the odd frame, the imaging signal by the green laser in the color sensitivity region 2 and the imaging signal by the red laser (680 nm) in the color sensitivity region 3 are output, and a deep-black imaging signal is output because there is no illumination light of the corresponding wavelength region in the color sensitivity region 1.

If the narrow-band light spectral intensity information ($\lambda$, P) is generated on the basis of this information, it is possible to separately detect light intensity information $P_4$ in the case where the image sensor 58 receives a reflected/scattered light of the illumination light of $\lambda_4$=630 nm in the color sensitivity region 3, and light intensity information $P_5$ in the case where the image sensor 58 receives a reflected/scattered light of the illumination light of $\lambda_5$=680 nm. In other words, the narrow-band lights included in the multiple narrow-band light color sensitivity region are turned on by different timings, and each image is independently obtained, so that each of the narrow-band lights can be separately detected, and the narrow-band light spectral intensity information ($\lambda$, P) can be independently obtained.

Figure 17:
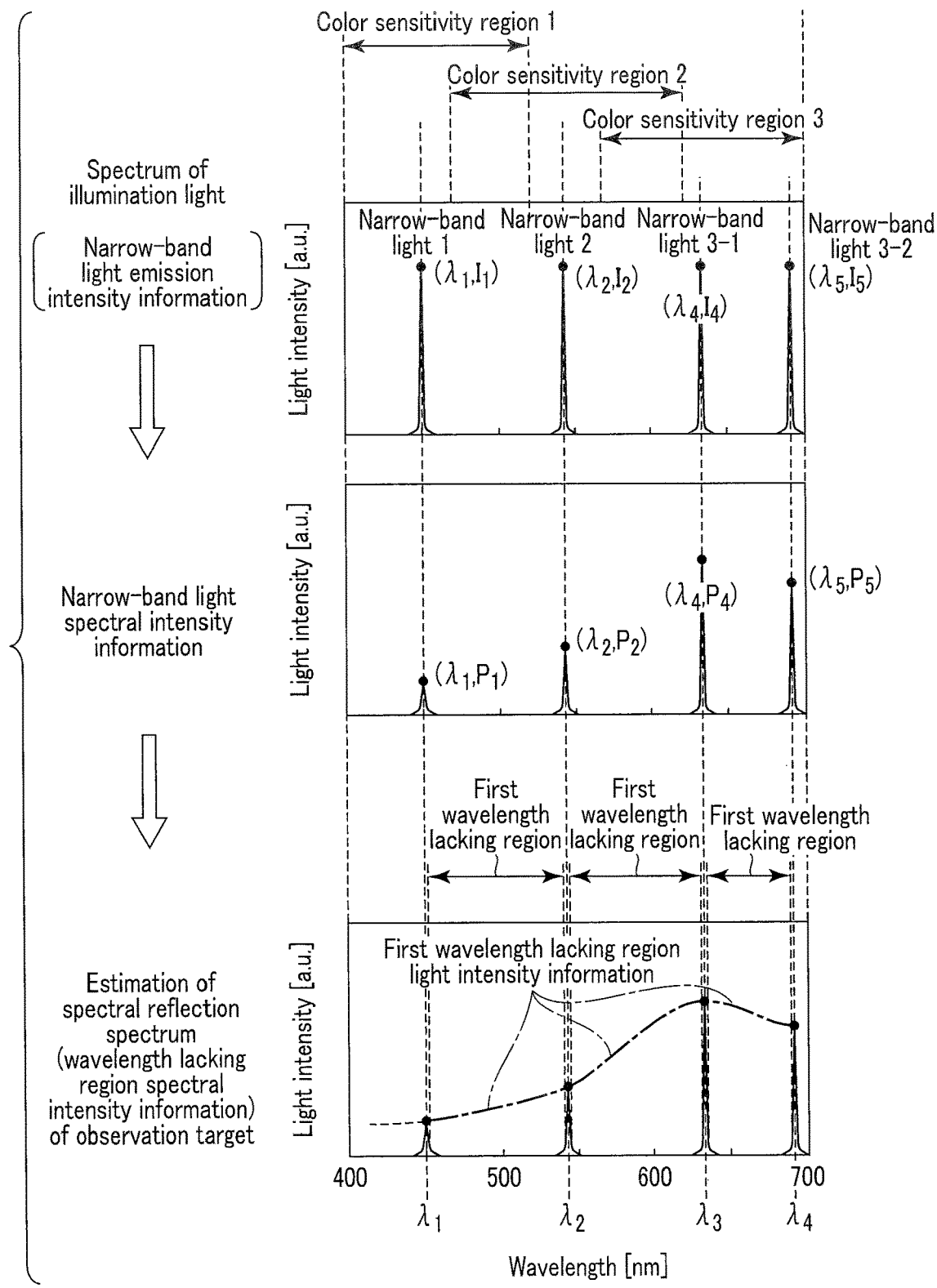
FIG. 17 shows the narrow-band light emission information, the narrow-band light spectral information, and the estimated first wavelength lacking region spectral intensity information in the third embodiment.

Consequently, the number of pieces of narrow-band light spectral intensity information ($\lambda$, P) in the present embodiment can be four that is greater than three that is the number of color sensitivity regions and that is the same as the number of semiconductor lasers (FIG. 17).

Regarding the operation of the image processing circuit 62 after the derivation of the narrow-band light spectral intensity information, the technique described in the first embodiment can be used. This allows estimating light intensity information for the wavelength lacking regions.

[Functions—Advantageous Effects]

As in the present embodiment, it is possible to derive the number of pieces of narrow-band light spectral intensity information ($\lambda$, P) that is greater than the number of color sensitivity regions of the image sensor 58 by properly setting the light emission timing of the light source. It is therefore possible to improve the estimation precision of the light intensity information for the wavelength lacking regions without using the special image sensor 58.

Although the semiconductor lasers 22A, 22B, 22D, and 22E emit lights by the timing shown in FIG. 16 in accordance with the frame timing of the image sensor 58 in the example shown in the present embodiment, the present invention is not limited to this. To provide the advantageous effects according to the present embodiment, it is only necessary to turn on/off the semiconductor lasers 22A, 22B, 22D, and 22E included in the same color sensitivity region by different timings. That is, the two semiconductor lasers 22A and 22B may be continuously turned on, and the sum of the outputs of the even frame and the odd frame may be the light intensity information $P_1$ and $P_2$. In this instance, the emission intensities $I_1$ and $I_2$ of the illumination lights may be reduced by half. This can reduce the load of the light source control circuit 30.

[Various Modifications]

[Modifications of Estimation of Light Intensity Information for Wavelength Lacking Regions]

The embodiments of the present invention only describe the smoothing technique based on the functional approximation for use as the method of estimating the light intensity information for the wavelength lacking regions to estimate a smooth and continuous curve, but the present invention is not limited to this.

Figure 18:
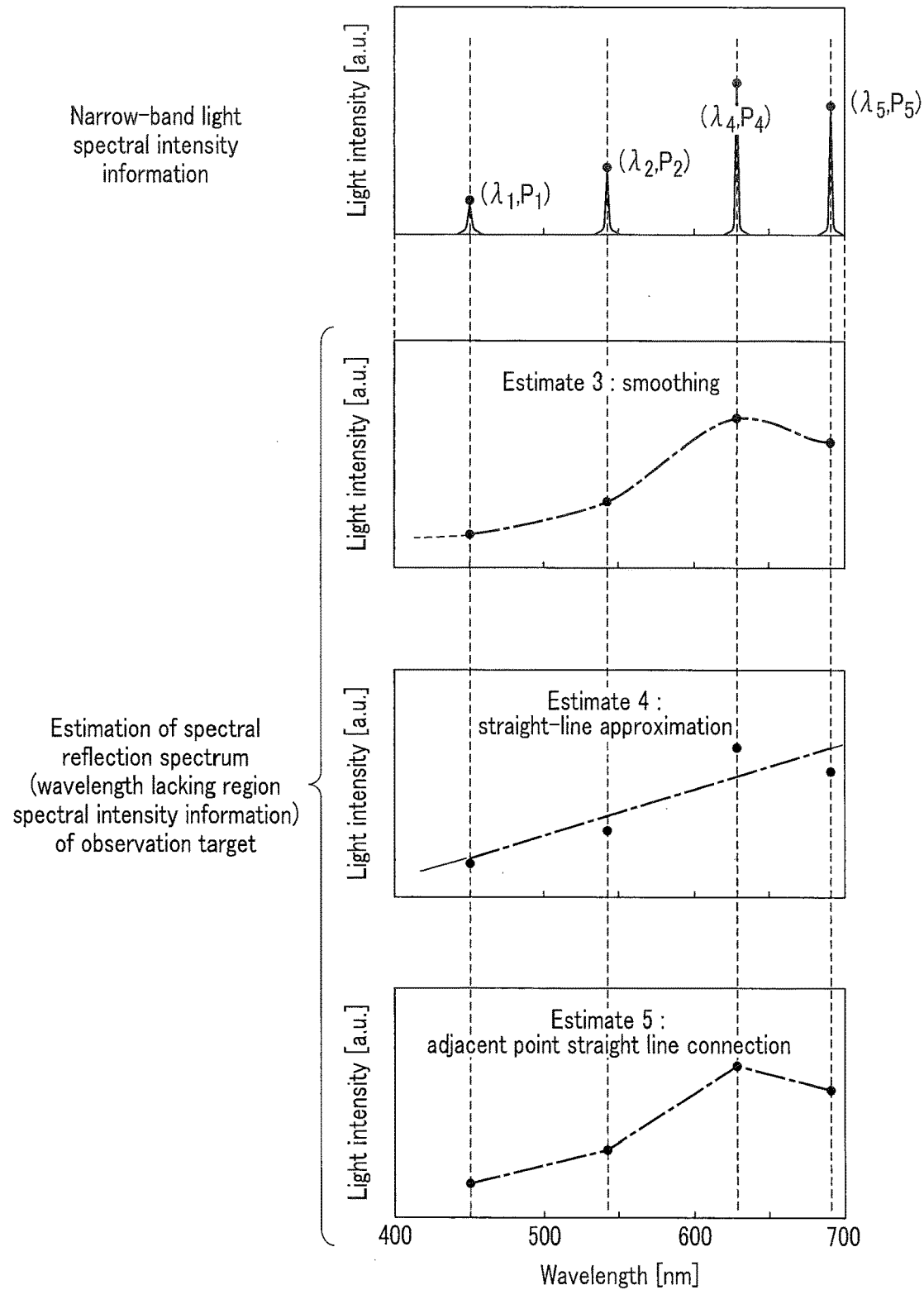
FIG. 18 shows estimation examples of the narrow-band light spectral information and the first wavelength lacking region spectral intensity information in a modification of the third embodiment.

For example, the light intensity information for the wavelength lacking regions can be estimated by several methods shown in FIG. 18. FIG. 18 shows estimation examples in which the narrow-band light spectral intensity information ($\lambda$, P) regarding the four narrow-band lights described in the third embodiment is obtained.

An example of smoothing that is the estimation method used in the first to third embodiments is shown as "Estimate 3" on the second section of FIG. 18. In contrast, an example of the estimation of the wavelength lacking regions by straight-line approximation is shown in "Estimate 4" on the third section of FIG. 18. For the technique of the straight-line approximation, commonly used various techniques can be used. For example, a least squares method may be used to calculate, for all the narrow-band lights, the square of the difference between the light intensity P of the obtained narrow-band light spectral intensity information ($\lambda$, P) and the intersection of a straight line and the wavelength $\lambda$ represented by a certain numerical expression, and find a function that represents a straight line to minimize the sum of the above.

It is possible to reduce the load of the image processing circuit 62 by estimating the wavelength lacking regions by the straight-line approximation as above. The arithmetic expression handled by the wavelength lacking region correction processor, in particular, is simplified, and it is therefore possible to obtain an image with relatively high color reproducibility by a relatively small-scale circuit configuration and program configuration. When the number of points of the narrow-band light spectral intensity information ($\lambda$, P) is small and when the points are scattered, smoothing is difficult, and there is a risk of obtaining wavelength lacking region light intensity information that is significantly different from actual one as an estimation result. In this case, the method by the straight-line approximation is particularly suitable because the risk of the increase of divergence from the actual wavelength lacking region light intensity information is low.

"Estimate 5" on the lowermost section of FIG. 18 shows an example of an estimation technique by adjacent point straight line connection such as a line graph in which adjacent coordinates of the narrow-band light spectral intensity information ($\lambda$, P) are connected with a straight line for the obtained narrow-band light spectral intensity information ($\lambda$, P). According to such an estimation method, for example, complicated processing does not need to be performed especially in the wavelength lacking region spectral intensity information estimator 64 in the image processing circuit 62, so that it is possible to reduce the load of the wavelength lacking region spectral intensity information estimator 64, and simplify the circuit scale and the program scale. In this instance, an estimated error in the wavelength lacking region spectral intensity information can be relatively suppressed. Therefore, according to the method of "Estimate 5", it is possible to achieve image processing such that the load of the wavelength lacking region spectral intensity information estimator 64 in the image processing circuit 62 is reduced, and yet an image having relatively high color reproducibility can be obtained.

[Modification of the Number of Narrow-Band Lights]

Although the number of color sensitivity regions is three and the number of narrow-band lights is the same or greater in all the cases described in the embodiments so far, the present invention is not limited to this. For example, even when the illumination lights only having two narrow-band lights exclusive of the narrow-band light 2 in the first embodiment shown in FIG. 19 are used, the reflected/scattered light by the observation target 90 in the wavelength lacking regions can be estimated on the basis of the techniques described so far.

Figure 19:
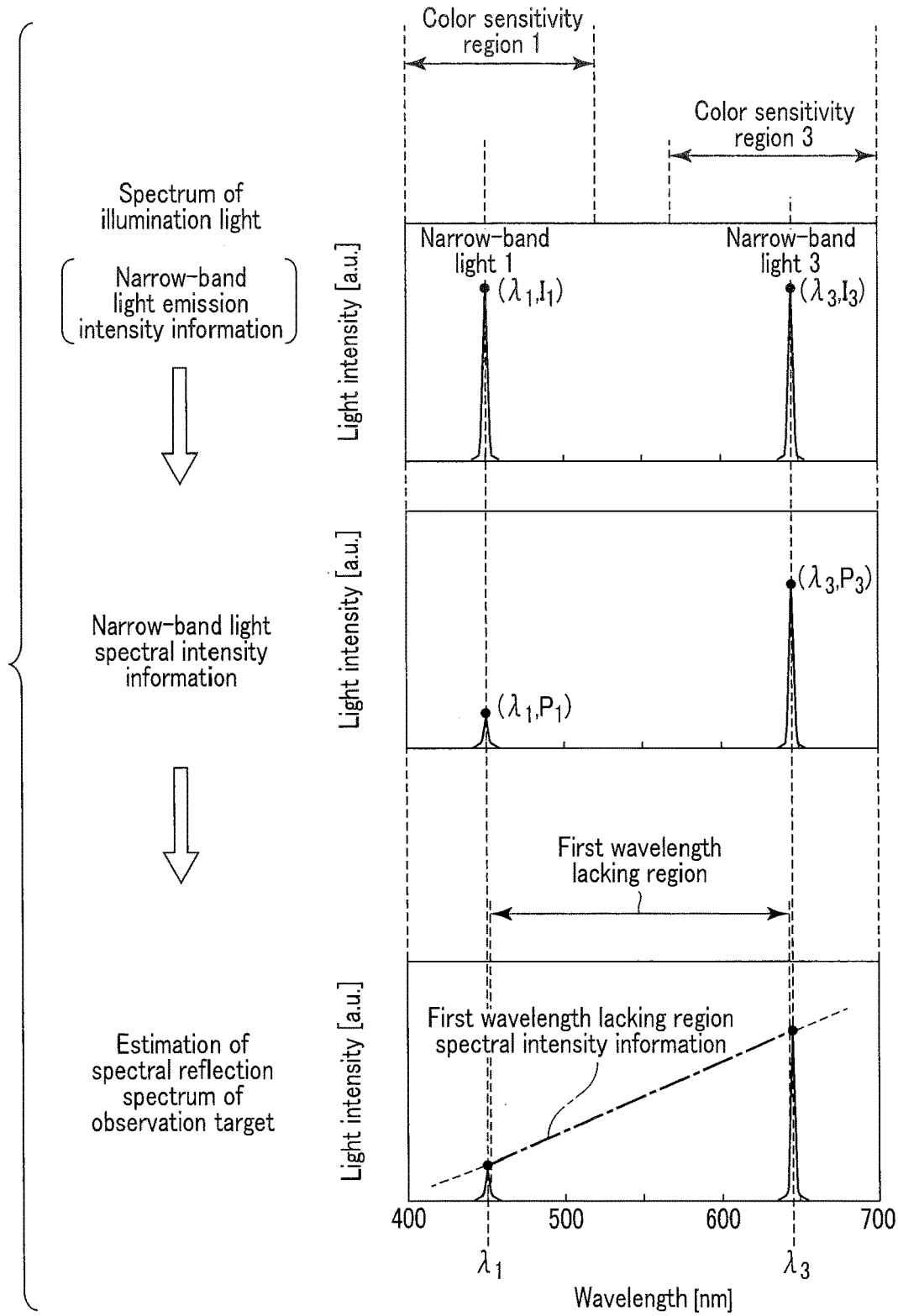
FIG. 19 shows the narrow-band light emission information, the narrow-band light spectral information, and the estimated first wavelength lacking region spectral intensity information in illumination lights exclusive of a narrow-band light 2 in the first embodiment.

As shown in FIG. 19, the spectrum of the illumination light comprises two narrow-band lights: the narrow-band light 1 having the narrow-band light spectral intensity information ($\lambda_1$, $\lambda_1$), and the narrow-band light 3 having the narrow-band light spectral intensity information ($\lambda_3$, $I_3$). The narrow-band light 1 is only included in the color sensitivity region 1, and the narrow-band light 3 is only included in the color sensitivity region 3, and there is no narrow-band light included in the color sensitivity region 2.

When such an illumination light is applied to the observation target 90, the reflected/scattered lights by the observation target 90 entering the image sensor 58 correspond to the narrow-band light spectral intensity information ($\lambda_1$, $I_1$) and the narrow-band light spectral intensity information ($\lambda_3$, $I_3$). On the basis of such information, the wavelength lacking region spectral intensity information estimator 64 estimates wavelength lacking region spectral intensity information. The wavelength lacking region spectral intensity information can be estimated by one of the estimation techniques described in the first to third embodiments.

The wavelength lacking region correction processor 66 performs the correction processing of the wavelength lacking regions in accordance with the above technique. In this instance, the light receiving intensity $P_{,\,detect}$ that is actually received by the light detection element corresponding to the color sensitivity region of the image sensor 58 is present in the color sensitivity region 1 and the color sensitivity region 3, but $P_{,\,detect}$ is not present in the color sensitivity region 2. Thus, the corrected light receiving amount information PP output from the wavelength lacking region correction processor 66 is exactly $P_{,\,estimate}$ regarding at least the color sensitivity region 2. $P_{,\,estimate}$ can be derived in accordance with, for example, the procedure described with reference to FIG. 9 in connection with the first embodiment.

Although the number of narrow-band lights is smaller than the number of color sensitivity regions in the case described here, the present invention is not limited to this. The present invention is applicable when the narrow-band lights equal in number to or greater in number than the color sensitivity regions are used but when there is a color sensitivity region having no narrow-band lights. For example, the wavelength lacking region correction processor can derive the corrected light receiving amount information PP in accordance with the procedure described above even when two narrow-band lights are included in the first color sensitivity region, one narrow-band light is included in the third color sensitivity region, and no narrow-band light is included in the second color sensitivity region.

[Modification of Light Source]

Although the multimode semiconductor laser is only used as the light source to radiate the narrow-band light in the example shown in the present embodiment, the present invention is not limited to this. It is possible to use various solid-state lasers, gas lasers, and a compound semiconductor laser combined with an SHG element, etc. It is also possible to use a superluminescent diode (SLD) and an LED. A light source in which an LED or a laser is combined with a fluorescent substance and that has wavelength lacking regions is also suitable.

If a single-mode laser is used, the peak wavelength of the narrow-band light is stably determined at one point, so that the value of λ of the narrow-band light spectral intensity information (λ, P) becomes stable, and the precision of spectral estimation improves. In contrast, the use of the multimode laser is advantageous to, for example, the illumination of a large space because a bright narrow-band light can be sent out.

It is also appropriate to use an observation apparatus using a compound light source system in which, for example, an LED and a laser are combined. FIG. 20 shows an example of illumination lights in which three LED elements are combined. As shown, there are wavelength lacking regions even in the case of multiple LEDs, but light intensity information for the wavelength lacking regions can be estimated by the technique described in the embodiments.

Although one light source radiates only one narrow-band light in the example shown in the embodiment according to the present embodiment, the present invention is not limited to this. For example, it is possible to use a light source portion capable of simultaneously emitting more than one narrow-band light, such as an He—Cd laser that is a three-primary-color (white-light) laser to simultaneously oscillate a blue laser light of 441.6 nm, a green laser light of 537.8 nm, and a red laser light of 636.0 nm. In this instance, in the configuration of the endoscope apparatus shown in FIG. 1 and others, the number of the semiconductor lasers 22A, 22B, . . . that are light sources disposed in the light source portion is different from the number of narrow-band lights sent out from the light source portion, and the number of narrow-band lights is always greater than the number of light sources.

[Optical Fiber]

Furthermore, although the multimode single-wire optical fiber alone is used as the optical fiber in the embodiments, the present invention is not limited to this. For example, a single-mode fiber can be used. Various optical fibers can also be used, such as a step-index optical fiber or a grated-index optical fiber, a plastic fiber, and a compound material type optical fiber having a plastic cladding and a glass core.

It is also possible to use a bundle fiber in which the above optical fibers are bundled, and a general film-type waveguide or a slab-type waveguide in which a waveguide is formed on a resin substrate or a semiconductor substrate with a refractive index distribution.

[Utilization Field]

The present invention is suited to the observation of the inside of a closed space in which external light is almost negligible. The present invention is particularly suitably used in an endoscope that is used for medical purposes and that is used in digestive organs, respiratory organs, the ear, nose and throat, and urinary organs. The medical endoscope has a relatively small number of the kinds of spectral reflection spectra of the observation target, and can easily estimate the spectral reflection spectrum of the wavelength lacking regions by various wavelength lacking region estimation techniques described in the embodiments. The present invention is also suited to industrially used endoscopes that are used in various inspections and investigations. In the case of the industrial endoscopes, apart of interest of the observation target needs to be easily viewed in distinction from other regions, and it is possible to estimate the spectral reflection factor of apart to notice such as a defect or a rust and display the part in distinction from other regions by estimating the spectral reflection factor of the wavelength lacking regions on the basis of a slight difference of the intensities of the reflected/scattered light in the narrow-band light region in accordance with various wavelength lacking region estimation techniques described in the embodiments.

The embodiments of the present invention are illustrative only, and various combinations and modifications can be made without departing from the sprit of the present invention.

[Supplementary Explanation of Spectral Reflection Spectrum]

The spectral reflection factor is described. A general color rendering index Ra is generally used as an index to convert color reproducibility into a numerical value. The general color rendering index is defined by Japanese Industrial Standard, JIS Z 8726 "Method of Specifying Color Rendering Properties of Light Sources". Color samples of 15 test colors different in spectral reflection factor are used to evaluate a color rendering index, and R1 to R15 are measured as color rendering indexes for the respective test colors. The test colors 1 to 8 corresponding to R1 to R8 are spectral reflection factors based on objects in nature, and the test colors corresponding to R9 to R14 are set as spectral reflection factors based on objects that are relatively high in chroma. The test color 15 corresponding to R15 is a color based on the skin of a Japanese.

The general color rendering index that is most widely used as the index of color reproducibility is the average value of R1 to R8, and widely used as a value that represents color reproducibility.

FIG. 21 shows spectra of spectral reflection factors of the test colors 1, 2, 3, 4, 5, and 6, and FIG. 22 shows spectra of spectral reflection factors of the test colors 7, 8, and 15. The spectral reflection factor referred to here represents, as a reflection factor (%) per wavelength, the rate at which a light is reflected when the light is applied to an object.

While the wavelength range that is on the horizontal axis is indicated from 350 nm in the ultraviolet region to 800 nm in the infrared region in FIG. 21, there is no sample in which the spectral reflection factor changes with the wavelength in steps in the range of 400 nm to 700 nm that is a general visible light region. The change rate of the spectral reflection factor remains at approximately 1%/nm even in the vicinity of 610 nm of the test color 8 and 590 nm of the test color 15 where the spectral reflection factor most sharply changes in the visible light region. As shown in Jpn. Pat. Appln. KOKAI Publication No. 10-286235, it is known that color reproducibility improves to a slight degree even if multiple laser lights different several nm in wavelength are used.

If the wavelength at which the spectral reflection factor considerably changes is defined as $\lambda_k$, $\lambda_k$=610 nm in the test color 8, and $\lambda_k$=590 nm in the test color 15 (FIG. 22).

As shown in FIG. 21 and FIG. 22, the spectral reflection factors in the test colors 1 to 8 and 15 change the most at $\lambda_k$ in the test colors 8 and 15, but the rate of these changes remains at approximately 1%/nm, and remains at gentle changes of approximately 0.5%/nm or less if the above two regions are excluded. That is, it is presumed that there are a few observation targets 90 in which the spectral reflection spectrum extremely changes, and the effect of color reproducibility improvements can be expected even if the wavelength lacking regions are interpolated by, for example, the smoothing described in the embodiments.

When the spectral reflection spectrum of the principal observation target is known, it is preferable for the wavelength of the laser as a narrow-band light source to put a peak wavelength $\lambda_{peak}$ across the wavelength $\lambda_k$ at which the spectral reflection spectrum considerably changes. According to such a configuration, the spectral reflection spectrum can be estimated even for an observation target having a sharp change in the spectral reflection spectrum even with illumination lacking in wavelength all over the place, and an image having high color reproducibility can be obtained.

In the meantime, it is self-evident that color reproducibility is higher in an observation apparatus capable of emitting more laser lights. That is, color reproducibility can be considerably increased if 100 or more laser lights can be arranged every several nm in the visible light region. However, the wavelengths of generally distributed laser light sources are limited to a particular region, and laser light sources having other wavelengths are unavailable or are expensive even if available. The use of a large number of laser light sources tends to result in high costs, and causes various problems such as high power consumption and a size increase. Therefore, the smallest possible number of laser light sources is preferable.

In view of the circumstances, in the present embodiment, the maximum number of laser light sources remains at four that is the minimum required number to obtain color reproducibility. However, it goes without saying that the number of laser light sources may be two or may be five or more in accordance with the required performance of the observation apparatus.

[Summary]

To sum up, observation apparatuses listed below are disclosed in the present description. In other words, the embodiments described above can be generalized as below.

[1] An observation apparatus to observe an internal space of an observation target, the observation apparatus comprising:

an insertion portion having a distal end to be inserted into the internal space;

a light exit that radiates an illumination light to the internal space surface and that is provided at the distal end;

an image sensor that detects a reflected/scattered light from the internal space surface to output an imaging signal and that is provided at the distal end;

an image processing circuit that processes the imaging signal to output an image signal; and a display that displays an image in accordance with the image signal, wherein the illumination light comprises narrow-band lights, wavelength regions detectable by the image sensor comprise narrow-band light regions in which the respective narrow-band lights are present, a first wavelength lacking region that is a region between the adjacent two narrow-band light regions, and a second wavelength lacking region that is a region outside the endmost two narrow-band light regions, the image sensor includes a large number of light detection elements including multiple kinds of light detection elements to detect lights in multiple color sensitivity regions, respectively, the image processing circuit includes a wavelength lacking region spectral intensity information estimator that associates, regarding each color sensitivity region, a peak wavelength of the narrow-band light included in the color sensitivity region with the intensity of the reflected/scattered light from the internal space surface detected by the light detection element corresponding to the color sensitivity region to derive narrow-band light spectral intensity information (wavelength $\lambda$, light receiving intensity P), and estimates wavelength lacking region spectral intensity information on the basis of the narrow-band light spectral intensity information, the wavelength lacking region spectral intensity information being intensity information regarding the reflected/scattered light from the internal space surface in the first wavelength lacking region, and the image processing circuit includes a wavelength lacking region correction processor that performs wavelength lacking region correction processing on the basis of the narrow-band light spectral intensity information and the wavelength lacking region spectral intensity information so that the image signal will be closer to an image signal obtained when an illumination light having no wavelength lacking regions is applied.

[2] The observation apparatus according to [1], wherein n is a natural number of 2 or more, and k is a natural number of 1 to n, both the number of the narrow-band lights and the number of the color sensitivity regions are n, and a narrow-band light is configured to be included in a color sensitivity region;

the narrow-band lights are first, second, . . . , and n-th narrow-band lights from a short wavelength side to a long wavelength side, and the color sensitivity regions are first, second, . . . , and n-th color sensitivity regions from the short wavelength side to the long wavelength side, in which case the k-th narrow-band light is included in the k-th color sensitivity region; and a peak wavelength of the k-th narrow-band light is $\lambda_k$, and the intensity of the reflected/scattered light from the internal space surface detected by the light detection element corresponding to the k-th color sensitivity region is $P_k$, in which case the narrow-band light spectral intensity information (wavelength $\lambda$, light receiving intensity P) is derived as $(\lambda_k, P_k)$.

[3] The observation apparatus according to [1], wherein n and m are natural numbers of 2 or more, i and j are natural numbers of 1 to n, and l is a natural number of 1 to m;

the number of the color sensitivity regions is n, the number of the narrow-band lights is more than n, and the color sensitivity regions are first, second, . . . , and n-th color sensitivity regions from a short wavelength side to a long wavelength side, in which case the color sensitivity region including only one narrow-band light among the color sensitivity regions is a single narrow-band light color sensitivity region, and the color sensitivity region including multiple narrow-band lights among the color sensitivity regions is a multiple narrow-band light color sensitivity region;

the color sensitivity region included in the single narrow-band light color sensitivity region is a j-th color sensitivity region, and the color sensitivity region included in the multiple narrow-band light color sensitivity region is an i-th (i≠j) color sensitivity region, in which case the narrow-band light included in the j-th color sensitivity region is a j-th narrow-band light; and the number of the narrow-band lights included in the i-th color sensitivity region is m, in which case them narrow-band lights included in the i-th color sensitivity region are (i–1)-th, . . . , and (i–m)-th narrow-band lights, respectively, so that a peak wavelength of the j-th narrow-band light is $\lambda_j$, and the intensity of the reflected/scattered light from the internal space surface detected by the light detection element corresponding to the j-th color sensitivity region is $P_j$, a peak wavelength of the (i–l)-th narrow-band light is $\lambda_{i-l}$, and the intensity of the reflected/scattered light from the internal space surface detected by the light detection element corresponding to the i-th color sensitivity region is $P_i$; and the narrow-band light spectral intensity information (wavelength $\lambda$, light receiving intensity P) is derived as $(\lambda_j, P_j)$ in the j-th color sensitivity region, and derived as $((\Sigma\lambda_{i-l})/m, P_i)$ in the i-th color sensitivity region.

[4] The observation apparatus according to [1], wherein n and m are natural numbers of 2 or more, i and j are natural numbers of 1 to n, and l is a natural number of 1 to m;

the number of the color sensitivity regions is n, the number of the narrow-band lights is more than n, and the color sensitivity regions are first, second, . . . , and n-th color sensitivity regions from a short wavelength side to a long wavelength side, in which case the color sensitivity region including only one narrow-band light among the color sensitivity regions is a single narrow-band light color sensitivity region, and the color sensitivity region including multiple narrow-band lights among the color sensitivity regions is a multiple narrow-band light color sensitivity region;

the color sensitivity region included in the single narrow-band light color sensitivity region is a j-th color sensitivity region, and the color sensitivity region included in the multiple narrow-band light color sensitivity region is an i-th (i≠j) color sensitivity region, in which case the narrow-band light included in the j-th color sensitivity region is a j-th narrow-band light; and the number of the narrow-band lights included in the i-th color sensitivity region is m, in which case the m narrow-band lights included in the i-th color sensitivity region are (i–l)-th (l=1 to m) narrow-band lights, respectively, so that the light exit is configured to radiate the (i–l)-th (l=1 to m) narrow-band lights by different timings, and the intensity P of the reflected/scattered light from the internal space surface detected by the light detection element corresponding to the i-th color sensitivity region is detected to separate $P_{i-l}$ (l=1 to m) synchronously with the emission of the (i–l)-th (l=1 to m) narrow-band lights, whereby the narrow-band light spectral intensity information (wavelength $\lambda$, light receiving intensity P) is derived as $(\lambda_j, P_j)$ in the j-th color sensitivity region, and derived as $(\lambda_{i-l}, P_i)$ (l=1 to m) in the i-th color sensitivity region.

[5] The observation apparatus according to any one of [1] to [4], wherein the narrow-band light regions are regions having a light amount equal to or more than half of the peak intensity of a light emission region of the narrow-band light, and the second wavelength lacking region is in the wavelength regions detectable by the image sensor, and includes a region on the long wavelength side than the narrow-band light region that is closest to the long wavelength side, and a region on the short wavelength side than the narrow-band light region that is closest to the short wavelength side.

[6] The observation apparatus according to [5], wherein the narrow-band lights are multimode or single-mode laser lights, and the wavelength regions detectable by the image sensor are wavelength lacking regions all over the place.

[7] The observation apparatus according to [6], wherein the wavelength regions detectable by the image sensor are so-called visible light regions of approximately 400 nm to approximately 700 nm, a short-wavelength-side boundary is determined by a sensitivity limit of the image sensor, and a long-wavelength-side boundary is determined by a lower limit wavelength of an infrared light cut by an infrared cutoff filter.

[8] The observation apparatus according to any one of [1] to [4], wherein the image processing circuit only uses information regarding a narrow-band light intensity derivation region among information regarding the imaging signals output from the image sensor to derive the intensity P of the narrow-band light spectral intensity information (wavelength $\lambda$, light receiving intensity P) as an average of intensity information for the reflected/scattered light corresponding to each wavelength $\lambda$ in the whole narrow-band light intensity derivation region.

[9] The observation apparatus according to [8], wherein the narrow-band light intensity derivation region is the whole imaging screen.

[10] The observation apparatus according to [8], wherein the narrow-band light intensity derivation region is a region in which regions located in the vicinity of an upper limit and a lower limit of a dynamic range of the image sensor are excluded from the whole imaging screen.

[11] The observation apparatus according to [8], wherein the narrow-band light intensity derivation region is a region located in the vicinity of the center of the imaging screen.

[12] The observation apparatus according to [8], wherein the narrow-band light intensity derivation region is a region where a combination of pieces of narrow-band light spectral intensity information (wavelength $\lambda$, light receiving intensity P) is in a predetermined ratio range or in a highest range on the imaging screen.

[13] The observation apparatus according to [8], further comprising an input section to specify the narrow-band light intensity derivation region.

[14] The observation apparatus according to any one of [1] to [4], wherein the image processing circuit uses information regarding narrow-band light intensity derivation regions among information regarding the imaging signals output from the image sensor to derive, for each of the narrow-band light intensity derivation regions, the intensity P of the narrow-band light spectral intensity information (wavelength $\lambda$, light receiving intensity P) as an average of intensity information for the reflected/scattered light corresponding to each wavelength $\lambda$ in each narrow-band light intensity derivation region.

[15] The observation apparatus according to [14], wherein the narrow-band light intensity derivation regions are unit pixels.

[16] The observation apparatus according to any one of [1] to [4], wherein the wavelength lacking region spectral intensity information estimator estimates spectral intensity information for the first wavelength lacking region on the basis of the narrow-band light spectral intensity information (wavelength $\lambda$, light receiving intensity P).

[17] The observation apparatus according to [16], wherein the wavelength lacking region spectral intensity information estimator estimates the wavelength lacking region spectral intensity information so that it continues smoothly in the whole first wavelength lacking region on the basis of the narrow-band light spectral intensity information (wavelength λ, light receiving intensity P).

[18] The observation apparatus according to [17], wherein the wavelength lacking region spectral intensity information estimator makes an estimate by functional approximation, e.g. linear function approximation, high-dimensional function approximation, and least squares approximation.

[19] The observation apparatus according to [16], wherein the wavelength lacking region spectral intensity information estimator estimates the wavelength lacking region spectral intensity information so as to connect adjacent narrow-band light spectral intensity information (wavelength λ, light receiving intensity P) with a straight line.

[20] The observation apparatus according to [2], wherein the wavelength lacking region spectral intensity information estimator estimates the light receiving intensity P as a constant value of $P_k$ regarding the whole k-th color sensitivity region.

[21] The observation apparatus according to [20], wherein the color sensitivity regions overlap one another, and when an overlap region of the k-th color sensitivity region and the (k+1)-th color sensitivity region is a sensitivity overlap region k, $P_k$ is used as an imaging signal of the k-th color sensitivity region, and $P_{k+1}$ is used as an imaging signal of the (k+1)-th color sensitivity region regarding the sensitivity overlap region k.

[22] The observation apparatus according to [20], wherein the color sensitivity regions overlap one another, and when an overlap region of the k-th color sensitivity region and the (k+1)-th color sensitivity region is a sensitivity overlap region k, an average of $P_k$ and $P_{k+1}$ is used regarding the sensitivity overlap region k.

[23] The observation apparatus according to any one of [14] to [22], wherein the wavelength lacking region spectral intensity information estimator estimates the wavelength lacking region spectral intensity information by extrapolation regarding the second wavelength lacking region.

[24] The observation apparatus according to any one of [1] to [4], wherein the wavelength lacking region correction processor calculates corrected light amount information PP for each color sensitivity region from the wavelength lacking region spectral intensity information estimated by the wavelength lacking region spectral intensity information estimator.

[25] The observation apparatus according to [24], wherein the wavelength lacking region correction processor estimates a light receiving amount received by the light detection element corresponding to the corresponding color sensitivity region when a light of the estimated wavelength lacking region spectral intensity information is received, and outputs the corrected light amount information PP as image information.

[26] The observation apparatus according to [25], wherein the wavelength lacking region correction processor integrates the estimated wavelength lacking region spectral intensity information, and estimates, as a light receiving amount, a value in which the integrated value is divided by the width of the corresponding wavelength region.

[27] The observation apparatus according to any one of [24] to [26], wherein the wavelength lacking region correction processor estimates a light receiving amount to be received by the light detection element corresponding to the color sensitivity region on the basis of the wavelength lacking region spectral intensity information, transmission spectrum information for a wavelength filter of the corresponding color sensitivity region, and/or wavelength spectral light receiving sensitivity information for the image sensor, and the wavelength lacking region correction processor outputs the light receiving amount as image information.

[28] An endoscope apparatus comprising the observation apparatus according to any one of [1] to [26].

[29] The observation apparatus according to [1], wherein n and m are natural numbers of 2 or more, i and j are natural numbers of 1 to n, and l is a natural number of 1 to m;

the number of the color sensitivity regions is n, the number of the narrow-band lights is more than n, and the color sensitivity regions are first, second, . . . , and n-th color sensitivity regions from a short wavelength side to a long wavelength side, in which case the color sensitivity region including only one narrow-band light among the color sensitivity regions is a single narrow-band light color sensitivity region, and the color sensitivity region including multiple narrow-band lights among the color sensitivity regions is a multiple narrow-band light color sensitivity region;

the color sensitivity region included in the single narrow-band light color sensitivity region is a j-th color sensitivity region, and the color sensitivity region included in the multiple narrow-band light color sensitivity region is an i-th (i≠j) color sensitivity region, in which case the narrow-band light included in the j-th color sensitivity region is a j-th narrow-band light; and the number of the narrow-band lights included in the i-th color sensitivity region is m, in which case the m narrow-band lights included in the i-th color sensitivity region are i–1-st, . . . , and (i–m)-th narrow-band lights, respectively, so that a peak wavelength of the j-th narrow-band light is $\lambda_j$, and the intensity of the reflected/scattered light from the internal space surface detected by the light detection element corresponding to the j-th color sensitivity region is $P_j$, and the light intensity of the (i–l)-th narrow-band light sent out from an exit window is $I_{i-l}$, whereby the narrow-band light spectral intensity information (wavelength λ, light receiving intensity P) is derived as $(\lambda_j, P_j)$ in the j-th color sensitivity region, and derived as $(\Sigma(\lambda_{i-l} \times I_{i-l})/(\Sigma I_{i-l}), P)$ in the i-th color sensitivity region.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope apparatus for observing an internal space of an observation target, the endoscope apparatus comprising:

an insertion portion comprising:

a distal end configured to be inserted into the internal space; and a light exit provided at the distal end, wherein the light exit is configured to radiate an illumination light to a surface defining the internal space, wherein the illumination light comprises narrow-band lights;

an image sensor provided at the distal end, wherein the image sensor is configured to:

detect a reflected/scattered light from the surface defining the internal space; and output an imaging signal based on the reflected/scattered light detected,
wherein wavelength regions detectable by the image sensor comprise:
  narrow-band light regions corresponding to wavelengths of the narrow-band lights;
  a first wavelength lacking region that is a region between two adjacent narrow-band light regions of the narrow-band light regions; and
  a second wavelength lacking region that is a region outside the endmost two narrow-band light regions of the narrow-band light regions, and
wherein the image sensor comprises multiple kinds of light detection elements configured to detect lights in multiple color sensitivity regions, respectively; and
an image processor configured to:
  associate, regarding each of the multiple color sensitivity regions, a peak wavelength of the narrow-band light included in the each of the multiple color sensitivity regions with intensity of the reflected/scattered light from the surface defining the internal space detected by the one of the multiple kinds of light detection elements corresponding to the each of the multiple color sensitivity regions region to derive narrow-band light spectral intensity information;
  estimate wavelength lacking region spectral intensity information based on the narrow-band light spectral intensity information, wherein the wavelength lacking region spectral intensity information is intensity information regarding the reflected/scattered light from the surface defining the internal space in the first wavelength lacking region; and
  perform wavelength lacking region correction processing on the imaging signal based on the narrow-band light spectral intensity information and the wavelength lacking region spectral intensity information to generate an image signal to approximate an image signal obtained when an illumination light having no wavelength lacking regions is applied.

2. The endoscope apparatus according to claim 1,
wherein n is a natural number of 2 or more, and k is a natural number of 1 to n,
wherein both the number of the narrow-band lights and the number of the color sensitivity regions are n,
wherein the narrow-band lights are configured to be included in the color sensitivity regions,
wherein the narrow-band lights are first, second, . . . , and n-th narrow-band lights from a short wavelength side to a long wavelength side, and
wherein the color sensitivity regions are first, second, . . . , and n-th color sensitivity regions from the short wavelength side to the long wavelength side,
in which case a k-th narrow-band light is included in a k-th color sensitivity region; and
a peak wavelength of the k-th narrow-band light is $\lambda_k$, and the intensity of the reflected/scattered light from the surface defining the internal space detected by the light detection element corresponding to the k-th light detection element is $P_k$,
in which case the narrow-band light spectral intensity information (wavelength $\lambda$, light receiving intensity P) is derived as $(\lambda_k, P_k)$.

3. The endoscope apparatus according to claim 1,
wherein n and m are natural numbers of 2 or more, i and j are natural numbers of 1 to n, and 1 is a natural number of 1 to m,
wherein the number of the color sensitivity regions is n,
wherein the number of the narrow-band lights is more than n, and
wherein the color sensitivity regions are first, second, . . . , and n-th color sensitivity regions from a short wavelength side to a long wavelength side,
in which case the color sensitivity region including only one narrow-band light among the color sensitivity regions is a single narrow-band light color sensitivity region,
a color sensitivity region including multiple narrow-band lights among the color sensitivity regions is a multiple narrow-band light color sensitivity region,
a color sensitivity region included in the single narrow-band light color sensitivity region is a j-th color sensitivity region,
a color sensitivity region included in the multiple narrow-band light color sensitivity region is an i-th (i≠j) color sensitivity region,
in which case the narrow-band light included in the j-th color sensitivity region is a j-th narrow-band light; and
the number of the narrow-band lights included in the i-th color sensitivity region is m,
in which case the m narrow-band lights included in the i-th color sensitivity region are (i−1)-th, . . . , and (i−m)-th narrow-band lights, respectively,
so that a peak wavelength of the j-th narrow-band light is $\lambda_j$, and the intensity of the reflected/scattered light from the internal space surface detected by the light detection element corresponding to the j-th color sensitivity region is $P_j$,
a peak wavelength of the (i−1)-th narrow-band light is $\lambda_{i-1}$, and the intensity of the reflected/scattered light from the internal space surface detected by the light detection element corresponding to the i-th color sensitivity region is $P_j$; and
the narrow-band light spectral intensity information (wavelength $\lambda$, light receiving intensity P) is
derived as $(\lambda_j, P_j)$ in the j-th color sensitivity region, and
derived as $((\Sigma\lambda_{i-1})/m, P_i)$ in the i-th color sensitivity region.

4. The endoscope apparatus according to claim 1,
wherein n and m are natural numbers of 2 or more, i and j are natural numbers of 1 to n, and 1 is a natural number of 1 to m,
wherein the number of the color sensitivity regions is n,
wherein the number of the narrow-band lights is more than n, and
wherein the color sensitivity regions are first, second, . . . , and n-th color sensitivity regions from a short wavelength side to a long wavelength side,
  in which case the color sensitivity region including only one narrow-band light among the color sensitivity regions is a single narrow-band light color sensitivity region, and
  a color sensitivity region including multiple narrow-band lights among the color sensitivity regions is a multiple narrow-band light color sensitivity region;
  a color sensitivity region included in the single narrow-band light color sensitivity region is a j-th color sensitivity region, and
  a color sensitivity region included in the multiple narrow-band light color sensitivity region is an i-th (i≠j) color sensitivity region,
  in which case the narrow-band light included in the j-th color sensitivity region is a j-th narrow-band light; and the number of the narrow-band lights included in the i-th color sensitivity region is m, in which case the m narrow-band lights included in the i-th color sensitivity region are (i−1)-th (l=1 to m) narrow-band lights, respectively, so that the light exit is configured to radiate the (i−1)-th (l=1 to m) narrow-band lights by different timings, and intensity P of the reflected/scattered light from the internal space surface detected by the light detection element corresponding to the i-th color sensitivity region is detected to separate $P_{i-1}$ (l=1 to m) synchronously with the radiating of the (i−1)-th (l=1 to m) narrow-band lights, whereby the narrow-band light spectral intensity information (wavelength λ, light receiving intensity P) is derived as $(\lambda_j, P_j)$ in the j-th color sensitivity region, and derived as $(\lambda_{i-1}, P_i)$ (l=1 to m) in the i-th color sensitivity region.

5. The endoscope apparatus according to claim 1, wherein the narrow-band light regions are regions having a light amount equal to or more than half of a peak intensity of a light emission region of the narrow-band light.

6. The endoscope apparatus according to claim 5, wherein the narrow-band lights are multimode or single-mode laser lights.

7. The endoscope apparatus according to claim 1, wherein the image processor is configured to:
only use information regarding a narrow-band light intensity derivation region among information regarding the imaging signal output from the image sensor to derive the intensity of the narrow-band light spectral intensity information as an average of intensity information for the reflected/scattered light corresponding to each wavelength in the whole narrow-band light intensity derivation region.

8. The endoscope apparatus according to claim 7, wherein the narrow-band light intensity derivation region is the whole of an imaging screen of the image sensor.

9. The endoscope apparatus according to claim 7, wherein the narrow-band light intensity derivation region is a part of an imaging screen of the image sensor, and is one of (a) a region in which regions located in the vicinity of an upper limit and a lower limit of a dynamic range of the image sensor are excluded from the whole of the imaging screen, (b) a region located in the vicinity of the center of the imaging screen, and (c) a region where a combination of pieces of narrow-band light spectral intensity information is in a predetermined ratio range or in a highest range on the imaging screen.

10. The endoscope apparatus according to claim 7, wherein the image processor is configured to specify the narrow-band light intensity derivation region based on an input to an input device.

11. The endoscope apparatus according to claim 1, wherein the image processor is configured to
use information regarding narrow-band light intensity derivation regions among information regarding the imaging signal output from the image sensor to derive intensity of the narrow-band light spectral intensity information for each of the narrow-band light intensity derivation regions of intensity information for the reflected/scattered light corresponding to each wavelength; and and when the narrow-band light intensity derivation region corresponding to each wavelength λ includes multiple pixel regions, derive the intensity as an average thereof.

12. The endoscope apparatus according to claim 1, wherein the processor is configured to:
estimate the wavelength lacking region spectral intensity information based on the narrow-band light spectral intensity information:
so that it continues smoothly in the whole of the first wavelength lacking region by functional approximation; or
so as to connect two adjacent narrow-band light spectral intensity information with a straight line.

13. The endoscope apparatus according to claim 2, wherein the image processor is configured to:
estimate the light receiving intensity P as a constant value of $P_k$ regarding the whole k-th color sensitivity region, the color sensitivity regions overlap one another, and
when an overlap region of the k-th color sensitivity region and the (k+1)-th color sensitivity region is a sensitivity overlap region k, estimate to use $P_k$ as an imaging signal of the k-th color sensitivity region and use $P_{k+1}$ as an imaging signal of the (k+1)-th color sensitivity region regarding the overlap sensitivity region k, or estimate as an average value of $P_k$ and $P_{k+1}$ regarding the sensitivity overlap region k.

14. The endoscope apparatus according to claim 11, wherein the image processor is configured to estimate the wavelength lacking region spectral intensity information by extrapolation regarding the second wavelength lacking region.

15. The endoscope apparatus according to claim 1, wherein the processor is configured to:
calculate a light receiving amount to be received by the light detection element corresponding to the corresponding color sensitivity region from the wavelength lacking region spectral intensity information estimated; and
output corrected light amount information for each color sensitivity region as image information.

16. A method for controlling an endoscope apparatus to observe an internal space of an observation target, the endoscope apparatus comprising:
an insertion portion comprising:
a distal end configured to be inserted into the internal space; and
a light exit provided at the distal end, wherein the light exit is configured to radiate an illumination light to a surface defining the internal space,
wherein the illumination light comprises narrow-band lights; and
an image sensor provided at the distal end, wherein the image sensor is configured to:
detect a reflected/scattered light from the surface defining the internal space; and
output an imaging signal based on the reflected/scattered light detected,
wherein wavelength regions detectable by the image sensor comprise:
narrow-band light regions corresponding to wavelengths of the narrow-band lights;
a first wavelength lacking region that is a region between two adjacent narrow-band light regions of the narrow-band light regions; and a second wavelength lacking region that is a region outside the endmost two narrow-band light regions of the narrow-band light regions, and wherein the image sensor comprises multiple kinds of light detection elements configured to detect lights in multiple color sensitivity regions, respectively, wherein the method comprises:
associating, regarding each of the multiple color sensitivity regions, a peak wavelength of the narrow-band light included in the each of the multiple color sensitivity regions with the intensity of the reflected/scattered light from the surface defining the internal space detected by the one of the multiple kinds of light detection elements corresponding to the each of the multiple color sensitivity regions region to derive narrow-band light spectral intensity information;

estimating wavelength lacking region spectral intensity information based on the narrow-band light spectral intensity information, wherein the wavelength lacking region spectral intensity information is intensity information regarding the reflected/scattered light from the surface defining the internal space in the first wavelength lacking region; and performing wavelength lacking region correction processing on the imaging signal based on the narrow-band light spectral intensity information and the wavelength lacking region spectral intensity information to generate an image signal to approximate an image signal obtained when an illumination light having no wavelength lacking regions is applied.

17. A non-transitory computer-readable storage medium storing instructions for controlling an endoscope apparatus to observe an internal space of an observation target, the endoscope apparatus comprising:
an insertion portion comprising:
a distal end configured to be inserted into the internal space; and
a light exit provided at the distal end, wherein the light exit is configured to radiate an illumination light to a surface defining the internal space,
wherein the illumination light comprises narrow-band lights; and
an image sensor provided at the distal end, wherein the image sensor is configured to:
detect a reflected/scattered light from the surface defining the internal space; and
output an imaging signal based on the reflected/scattered light detected,
wherein wavelength regions detectable by the image sensor comprise:
narrow-band light regions corresponding to wavelengths of the narrow-band lights;
a first wavelength lacking region that is a region between two adjacent narrow-band light regions of the narrow-band light regions; and
a second wavelength lacking region that is a region outside the endmost two narrow-band light regions of the narrow-band light regions, and
wherein the image sensor comprises multiple kinds of light detection elements configured to detect lights in multiple color sensitivity regions, respectively,
wherein the instructions cause a computer to at least perform:
associating, regarding each of the multiple color sensitivity regions, a peak wavelength of the narrow-band light included in the each of the multiple color sensitivity regions with the intensity of the reflected/scattered light from the surface defining the internal space detected by the one of the multiple kinds of light detection elements corresponding to the each of the multiple color sensitivity regions region to derive narrow-band light spectral intensity information;
estimating wavelength lacking region spectral intensity information based on the narrow-band light spectral intensity information, wherein the wavelength lacking region spectral intensity information is intensity information regarding the reflected/scattered light from the surface defining the internal space in the first wavelength lacking region; and
performing wavelength lacking region correction processing on the imaging signal based on the narrow-band light spectral intensity information and the wavelength lacking region spectral intensity information to generate an image signal to approximate an image signal obtained when an illumination light having no wavelength lacking regions is applied.

* * * * *